United States Patent
Yasuda et al.

[11] Patent Number: 6,114,546
[45] Date of Patent: Sep. 5, 2000

[54] AMINOMETHYLENE DERIVATIVES AND ULTRAVIOLET ABSORBENT COMPRISING THEREOF

[75] Inventors: Heinosuke Yasuda; Naohiko Hukuoka, both of Koube, Japan

[73] Assignee: Chemipro Kasei Kaisha, Limited, Koube, Japan

[21] Appl. No.: 09/269,401

[22] PCT Filed: Oct. 3, 1997

[86] PCT No.: PCT/JP97/03536

§ 371 Date: Mar. 26, 1999

§ 102(e) Date: Mar. 26, 1999

[87] PCT Pub. No.: WO98/14423

PCT Pub. Date: Apr. 6, 1998

[30] Foreign Application Priority Data

Oct. 4, 1996 [JP] Japan .................................. 8-283345
Oct. 18, 1996 [JP] Japan .................................. 8-297277
Oct. 29, 1996 [JP] Japan .................................. 8-303697
May 27, 1997 [JP] Japan .................................. 9-152909
Jun. 19, 1997 [JP] Japan .................................. 9-179052

[51] Int. Cl.$^7$ ................................................ C07D 311/56
[52] U.S. Cl. ........................ 549/285; 544/302; 549/274; 568/376
[58] Field of Search ............................................. 549/285

[56] References Cited

FOREIGN PATENT DOCUMENTS 3-38554  2/1991  Japan .
7-89901  4/1995  Japan .

OTHER PUBLICATIONS

Uray, G. et al., "β, β–Diacyl–enamine Und–enole," Journal of Molecular Structure, 54, 1979, pp. 77–88.

*Primary Examiner*—Richard L. Raymond
*Assistant Examiner*—Venkataraman Balasubramanian
*Attorney, Agent, or Firm*—Oliff & Berridge, PLC

[57] ABSTRACT

The present invention provides an aminomethylene derivative represented by general formula (I):

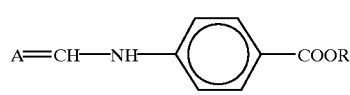

(I)

wherein A is a cyclic oxo group selected from the group consisting of following general formulae (a), (b), (c), (d) and (e):

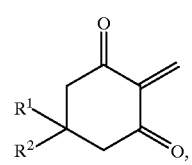

(a)

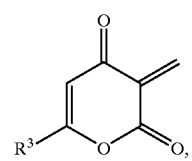

(b)

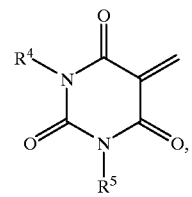

(c)

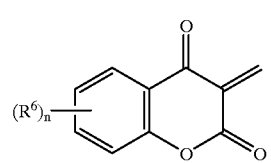

(d)

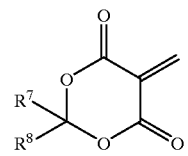

(e)

wherein $R^1$, $R^2$, $R^3$, $R^4$ and $R^5$ each independently represent H, an alkyl group or the like; $R^6$, $R^7$ and $R^8$ each independently represent an alkyl group or the like; $R^1$ and $R^2$ or $R^7$ and $R^8$ may combine with each other to form a tetramethylene group or the like; R represents an alkyl group optionally containing OH or O; and n is an integer of 0 to 4, a process for the same, and the use thereof. The derivatives have an excellent ultraviolet absorption ability and a high optical stability.

3 Claims, No Drawings

AMINOMETHYLENE DERIVATIVES AND ULTRAVIOLET ABSORBENT COMPRISING THEREOF

This application is a 371 of PCT/JP97/03536, filed Oct. 3, 1997.

TECHNICAL FIELD

The present invention relates to aminomethylene derivatives having excellent ultraviolet absorptivity and high light stability, and ultraviolet absorbent, cosmetic materials and weatherproofing polymer composition comprising thereof, and methods for producing above described aminomethylene derivatives.

PRIOR ART

It has been known that organic substances, especially polymer compounds, are subjected to yellowing, discoloration, cracking or embrittlement by the action of ultraviolet rays. Meanwhile, ultraviolet rays that reach to the ground surface consist mostly of UV-B (280 to 320 nm) and UV-A (320 to 400 nm). Among them, ultraviolet rays of the UV-A range, when more than a certain amount of them is applied to the skin, cause rash or blisters and are also considered to causes lowering of elasticity or browning of the skin. In order to prevent such changes of the skin caused by ultraviolet rays of the UV-A range, so called sunscreen cosmetics which contain ultraviolet absorbent are known. As known ultraviolet absorbents that have been used there are benzophenone derivatives including 4-phenylbenzophenone and 2-hydroxy-4-methoxybenzophenone-5-sulfonic acid, dibenzoylmethane derivatives including 4-tert-butyl-4'-methoxydibenzoylmethane, and benzotriazole derivatives including 2-(2-hydroxy-5-methoxyphenyl)benzotriazole.

Above described conventional synthetic compounds which are used as ultraviolet absorbent for UV-A in organic substances, especially in polymer compounds, have defect that they react with metal ions and cause coloring. Further, since ultraviolet absorbents themselves are colored in general, the amount of use is restricted. On the other hand, conventionally known synthetic compounds used as UV-A absorbents which are usually added to cosmetic materials and others, have limits on the amount can be used because of their irritativeness to the skin, and therefore, they cannot be used at the sufficient amount required for protecting the skin from sunburn and can provide only smaller UV-A protection effect. Therefore, development of a synthetic compound that absorbs ultraviolet rays of the UV-A range and shows much high absorption, in other words has higher molecular absorptivity, has been expected.

OBJECT OF THE INVENTION

The primary object of the present invention is to provide a novel compound showing much high absorption, in other words has higher molecular absorptivity, and a method for producing the same.

The second object of the present invention is to provide a novel ultraviolet absorbent through utilizing above described ultraviolet absorptivity, a cosmetic material and a weatherproofing organic polymer composition including thereof.

DISCLOSURE OF THE INVENTION

The first aspect of the present invention relates to an aminomethylene derivative represented by general formula (I):

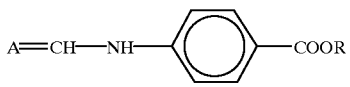
(I)

in which A is a cyclic oxo group selected from the group consisting of following general formulae (a), (b), (c), (d) and (e),

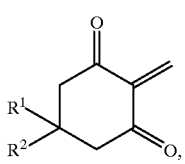
(a)

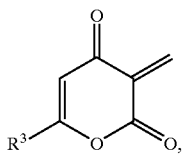
(b)

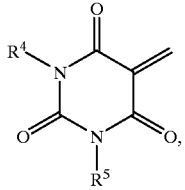
(c)

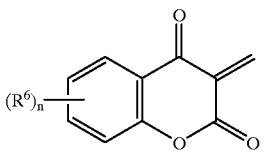
(d)

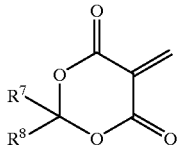
(e)

wherein $R^1$, $R^2$, $R^3$, $R^4$ and $R^5$ each independently are groups selected from the group consisting of a hydrogen atom, linear or branched, saturated or unsaturated alkyl groups, cycloalkyl groups, aralkyl groups and aryl groups, $R^6$ is a group selected from the group consisting of linear or branched, saturated or unsaturated alkyl groups, cycloalkyl groups, aralkyl groups, aryl groups, a hydroxyl group, alkoxy groups, alkoxycarbonyl groups, acyl groups, an amino group, acylamino groups, alkylamino groups, dialkylamino groups, arylamino groups and halogens, $R^7$ and $R^8$ each independently are groups selected from the group consisting of linear or branched, saturated or unsaturated alkyl groups, cycloalkyl groups, aralkyl groups and aryl groups, further $R^1$ and $R^2$ or $R^7$ and $R^8$ can, together, form a tetramethylene group, pentamethylene group or hexamethylene group, and R is a group selected from the group consisting of linear or branched, saturated or unsaturated alkyl groups, aralkyl groups, aryl groups, cycloalkyl groups, alkyl groups containing hydroxyl group, alkoxycarbonylalkylene groups and alkyl groups containing oxygen atom, and n is an integer of 0 to 4 wherein when n is 2 or more, each of plural $R^6$s can be different groups within above described groups.

The second aspect of the present invention relates to an ultraviolet absorbent containing said aminomethylene derivative.

The third aspect of the present invention relates to a cosmetic material containing said aminomethylene derivative.

The fourth aspect of the present invention relates to a weatherproofing organic polymer composition containing said aminomethylene derivative.

The fifth aspect of the present invention relates to a method for producing an aminomethylene derivative represented by following general formula (I):

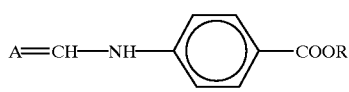
(I)

wherein A is a cyclic oxo group selected from the group consisting of following general formulae (a), (b), (c), (d) and (e):

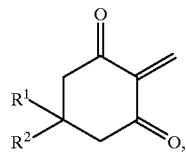
(a)

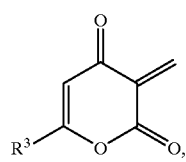
(b)

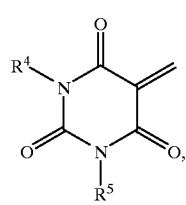
(c)

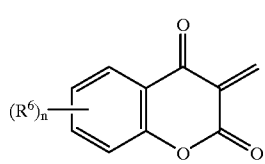
(d)

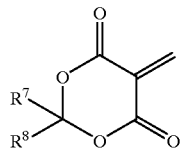
(e)

wherein $R^1$, $R^2$, $R^3$, $R^4$ and $R^5$ each independently are groups selected from the group consisting of a hydrogen atom, linear or branched, saturated or unsaturated alkyl groups, cycloalkyl groups, aralkyl groups and aryl groups, $R^6$ is a group selected from the group consisting of linear or branched, saturated or unsaturated alkyl groups, cycloalkyl groups, aralkyl groups, aryl groups, a hydroxyl group, alkoxy groups, alkoxycarbonyl groups, acyl groups, an amino group, acylamino groups, alkylamino groups, dialkylamino groups, arylamino groups and halogens, $R^7$ and $R^8$ each independently are groups selected from the group consisting of linear or branched, saturated or unsaturated alkyl groups, cycloalkyl groups, aralkyl groups and aryl groups, further $R^1$ and $R^2$ or $R^7$ and $R^8$ can, together, form a tetramethylene group, pentamethylene group or hexamethylene group, and R is a group selected from the group consisting of linear or branched, saturated or unsaturated alkyl groups, aralkyl groups, aryl groups, cycloalkyl groups, alkyl groups containing hydroxyl group, alkoxycarbonylalkylene groups and alkyl groups containing oxygen atom, and n is an integer of 0 to 4 wherein when n is 2 or more, each of plural $R^6$s can be different groups within above described groups, characterised in that a cyclic oxo compound represented by the general formula (II):

A' (II)

wherein A' is a compound selected from the group consisting of following general formulae (a'), (b'), (c'), (d') and (e'):

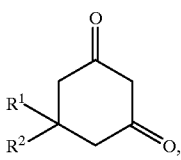
(a')

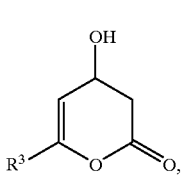
(b')

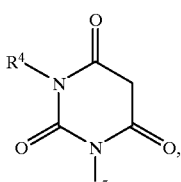
(c')

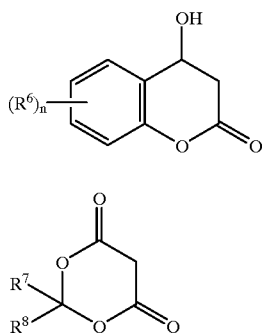

(d')

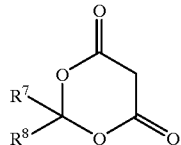

(e')

wherein $R^1$, $R^2$, $R^3$, $R^4$ and $R^5$ each independently are groups selected from the group consisting of an hydrogen atom, linear or branched, saturated or unsaturated alkyl groups, cycloalkyl groups, aralkyl groups and aryl groups, $R^6$ is a group selected from the group consisting of linear or branched, saturated or unsaturated alkyl groups, cycloalkyl groups, aralkyl groups, aryl groups, a hydroxyl group, alkoxy groups, alkoxycarbonyl groups, acyl groups, an amino group, acylamino groups, alkylamino groups, dialkylamino groups, arylamino groups and halogens, $R^7$ and $R^8$ each independently are groups selected from the group consisting of linear or branched, saturated or unsaturated alkyl groups, cycloalkyl groups, aralkyl groups and aryl groups, further $R^1$ and $R^2$ or $R^7$ and $R^8$ can, together form a tetramethylene group, pentamethylene group or hexamethylene group, and n is an integer of 0 to 4 wherein when n is 2 or more, each of plural $R^6$s can be different groups within above described groups, is allowed to react with an N-formylamino benzoate derivative represented by general formula (III):

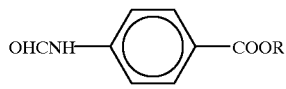

(III)

wherein R is a group selected from the group consisting of linear or branched, saturated or unsaturated alkyl groups, cycloalkyl groups, aralkyl groups, aryl groups, alkyl groups containing hydroxyl group, alkoxycarbonylalkylene groups and alkyl groups containing oxygen atom, in organic solvent and in the presence of an acid catalyst.

Regarding to $R^1$, $R^2$, $R^3$, $R^4$ and $R^5$, examples of linear or branched, saturated or unsaturated alkyl groups include methyl, ethyl, propyl, isopropyl, butyl, isobutyl, or allyl groups but those having 1 to 8 carbon atoms are preferable. Examples of above described cycloalkyl groups include cyclopentyl and cyclohexyl. Examples of above described aralkyl groups include those of which one hydrogen of said alkyl groups is substituted by a phenyl group, such as phenylethyl and phenylpropyl groups. Examples of above described aryl groups include a phenyl group and phenyl groups substituted by methyl, methoxy, ethoxy, methoxycarbonyl, ethoxycarbonyl, halogen, acetyl, cyano group or the like.

Regarding to $R^6$, examples of above described linear or branched, saturated or unsaturated alkyl groups include methyl, ethyl, n-propyl, isopropyl, n-butyl, isobutyl, t-butyl, allyl, but those having 1 to 8 carbon atoms are preferable. Examples of above described cycloalkyl groups include cyclopentyl and cyclohexyl groups. Examples of above described aralkyl groups include those of which one hydrogen of said alkyl groups is substituted by a phenyl group, such as benzyl, phenylethyl and phenylpropyl groups. Examples of above described aryl groups include a phenyl group and phenyl groups substituted by alkyl groups such as methyl and ethyl, alkoxyl groups such as methoxy and ethoxy, alkoxycarbonyl groups such as methoxycarbonyl and ethoxycarbonyl, or other substituent such as a halogen, acetyl and cyano.

Examples of above described alkoxy groups include methoxy group, ethoxy group, n-propoxy group, isopropoxy group and n-butoxy group. Examples of above described alkoxycarbonyl groups include methoxycarbonyl group and ethoxycarbonyl group. Examples of above described acyl groups include acetyl group, n-propionyl group and isopropionyl group. Examples of above described acylamino groups include acetylamino group and n-propionylamino group. Examples of above described alkylamino groups include amino groups having above described alkyl groups, such as methylamino group and ethylamino group. Examples of above described dialkylamino groups include dimethylamino group and diethylamino group. Examples of above described arylamino groups include amino groups having above described aryl groups, such as phenylamino group, tolylamino group, anisylamino group.

Regarding $R^7$ and $R^8$, examples of above described linear or branched, saturated or unsaturated alkyl groups include methyl, ethyl, n-propyl, isopropyl, n-butyl, isobutyl and allyl groups, but those having 1 to 8 carbon atoms are preferable. Examples of above described cycloalkyl groups include cyclopentyl and cyclohexyl groups. Examples of above described aralkyl groups include those of which one hydrogen of said alkyl groups is substituted by a phenyl group, such as phenylethyl and phenylpropyl groups. Examples of above described aryl groups include a phenyl group and phenyl groups substituted by methyl, methoxy, ethoxy, methoxycarbonyl, ethoxycarbonyl, halogen, acetyl, cyano or the like.

Further $R^1$ and $R^2$ or $R^7$ and $R^8$ can, together form a tetramethylene group, pentamethylene group or hexamethylene group.

Regarding R, examples of above described linear or branched, saturated or unsaturated alkyl groups include methyl group, ethyl group, n-propyl group, isopropyl group, n-butyl group, isobutyl group, sec-butyl group, tert-butyl group, n-pentyl group, n-hexyl group, n-heptyl group, 2-ethylhexyl group, n-octyl group, n-nonyl group, isononyl group, n-decyl group, n-undecyl group, n-dodecyl group, n-tridecyl group, iso-tridecyl group, n-tetradecyl group, n-pentadecyl group, n-hexadecyl group, n-heptadecyl group, n-octadecyl group, n-eicosyl group, allyl group and propene group, but those having carbon atoms of 1 to 20 are preferable. Longer alkyl groups also can be used, in that case, synthesis is performed using oxo process or the Ziegler process. Examples of above described aralkyl groups, cycloalkyl groups and aryl groups can be the same with the examples described regarding to $R^1$ and $R^2$. Examples of above described alkyl group having hydroxyl group includes methylol group and ethylol group. Examples of above described alkoxycarbonylalkylene groups include methoxycarbonylmethyl group, ethoxycarbonylmethyl group and 2-ethylhexyloxylcarbonylmethyl group. Examples of above described alkyl groups having oxygen atom include methoxyethyl group, ethoxyethyl group and methoxyethyloxy group.

Above described reaction is generally performed at a temperature range of 10 to 60° C., preferably 30 to 50° C., and examples of organic solvent used for the reaction can be any solvent that dissolves compounds represented by the general formula (I) and (II), respectively and include aromatic hydrocarbons and halogenated alkyls, such as toluene, xylene, dichloroethylene and chloroform.

Examples of above described acid catalyst include phosphorus pentachloride, phosphorus trichloride, phosphorus oxychloride, thionyl chloride and sulfuryl chloride.

Organic materials stabilized by the compound represented by the general formula (I), for example cosmetic materials and polymer materials, can further include conventionally used additives such as an antioxidant, light stabilizing agent, metal deactivator and peroxide scavenger.

Said organic materials may be natural or synthetic polymers, for example cellulose, CMC, natural rubbers, synthetic rubbers such as SBR, NBR or the like, polyolefins such as polyethylene, polypropylene or the like, synthetic resins such as polyester, polyamide, polyurethane, polyvinyl chloride or the like, and so on.

Of the aminomethylene derivatives represented by the general formula (I) used in the present invention, concrete examples of aminomethylenecyclohexane derivatives in which A in the formula (I) is (a), represented by the formula (Ia):

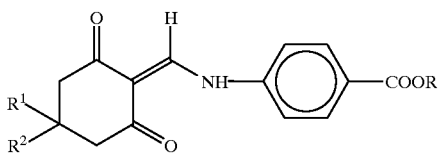

(Ia)

wherein $R^1$, $R^2$ and R are as defined above, include following compounds:

2-(4-ethoxycarbonylphenylamino)-methylene-1,3-cyclohexadione;
2-(4-isopropoxycarbonylphenylamino)-methylene-1,3-cyclohexadione;
2-(4-isobutoxycarbonylphenylamino)-methylene-1,3-cyclohexadione;
2-(4-sec-butoxycarbonylphenylamino)-methylene-1,3-cyclohexadione;
2-(4-tert-butoxycarbonylphenylamino)-methylene-1,3-cyclohexadione;
2-(4-n-pentyloxycarbonylphenylamino)-methylene-1,3-cyclohexadione;
2-(4-n-hexyloxycarbonylphenylamino)-methylene-1,3-cyclohexadione;
2-(4-n-heptyloxycarbonylphenylamino)-methylene-1,3-cyclohexadione;
2-(4-n-nonyloxycarbonylphenylamino)-methylene-1,3-cyclohexadione;
2-(4-n-decyloxycarbonylphenylamino)-methylene-1,3-cyclohexadione;
2-(4-n-undecyloxycarbonylphenylamino)-methylene-1,3-cyclohexadione;
2-(4-n-dodecyloxycarbonylphenylamino)-methylene-1,3-cyclohexadione;
2-(4-n-tridecyloxycarbonylphenylamino)-methylene-1,3-cyclohexadione;
2-(4-n-tetradecyloxycarbonylphenylamino)-methylene-1,3-cyclohexadione;
2-(4-n-pentadecyloxycarbonylphenylamino)-methylene-1,3-cyclohexadione;
2-(4-n-hexadecyloxycarbonylphenylamino)-methylene-1,3-cyclohexadione;
2-(4-n-heptadecyloxycarbonylphenylamino)-methylene-1,3-cyclohexadione;
5,5-dimethyl-2-(4-ethoxycarbonylphenylamino)-methylene-1,3-cyclohexadione;
5,5-dimethyl-2-(4-isopropoxycarbonylphenylamino)-methylene-1,3-cyclohexadione;
5,5-dimethyl-2-(4-isobutoxycarbonylphenylamino)-methylene-1,3-cyclohexadione;
5,5-dimethyl-2-(4-sec-butoxycarbonylphenylamino)-methylene-1,3-cyclohexadione;
5,5-dimethyl-2-(4-tert-butoxycarbonylphenylamino)-methylene-1,3-cyclohexadione;
5,5-dimethyl-2-(4-n-pentyloxycarbonylphenylamino)-methylene-1,3-cyclohexadione;
5,5-dimethyl-2-(4-n-hexyloxycarbonylphenylamino)-methylene-1,3-cyclohexadione;
5,5-dimethyl-2-(4-n-heptyloxycarbonylphenylamino)-methylene-1,3-cyclohexadione;
5,5-dimethyl-2-(4-n-nonyloxycarbonylphenylamino)-methylene-1,3-cyclohexadione;
5,5-dimethyl-2-(4-n-decyloxycarbonylphenylamino)-methylene-1,3-cyclohexadione;
5,5-dimethyl-2-(4-n-undecyloxycarbonylphenylamino)-methylene-1,3-cyclohexadione;
5,5-dimethyl-2-(4-n-dodecyloxycarbonylphenylamino)-methylene-1,3-cyclohexadione;
5,5-dimethyl-2-(4-n-tridecyloxycarbonylphenylamino)-methylene-1,3-cyclohexadione;
5,5-dimethyl-2-(4-n-tetradecyloxycarbonylphenylamino)-methylene-1,3-cyclohexadione;
5,5-dimethyl-2-(4-n-pentadecyloxycarbonylphenylamino)-methylene-1,3-cyclohexadione;
5,5-dimethyl-2-(4-n-hexadecyloxycarbonylphenylamino)-methylene-1,3-cyclohexadione;
5,5-dimethyl-2-(4-n-heptadecyloxycarbonylphenylamino)-methylene-1,3-cyclohexadione;
5,5-diethyl-2-(4-methoxycarbonylphenylamino)-methylene-1,3-cyclohexadione;
5,5-diethyl-2-(4-ethoxycarbonylphenylamino)-methylene-1,3-cyclohexadione;
5,5-diethyl-2-(4-n-propoxycarbonylphenylamino)-methylene-1,3-cyclohexadione;
5,5-diethyl-2-(4-isopropoxycarbonylphenylamino)-methylene-1,3-cyclohexadione;
5,5-diethyl-2-(4-n-butoxycarbonylphenylamino)-methylene-1,3-cyclohexadione;
5,5-diethyl-2-(4-n-pentyloxycarbonylphenylamino)-methylene-1,3-cyclohexadione;
5,5-diethyl-2-(4-n-hexyloxycarbonylphenylamino)-methylene-1,3-cyclohexadione;
5,5-diethyl-2-(4-n-heptyloxycarbonylphenylamino)-methylene-1,3-cyclohexadione;
5,5-diethyl-2-[4-(2-ethylhexyloxycarbonylphenylamino)]-methylene-1,3-cyclohexadione;
5,5-diethyl-2-(4-n-octadecyloxycarbonylphenylamino)-methylene-1,3-cyclohexadione;
5,5-dimethyl-2-(4-methoxyethylcarbonylphenylamino)-methylene-1,3-cyclohexadione;
5,5-dimethyl-2-(4-ethoxyethylcarbonylphenylamino)-methylene-1,3-cyclohexadione;
5,5-dimethyl-2-(4-methoxycarbomethyloxycarbonylphenylamino)-methylene-1,3-cyclohexadione;
5,5-dimethyl-2-(4-ethoxycarbomethyloxycarbonylphenylamino)-methylene-1,3-cyclohexadione;
5,5-diethyl-2-(4-methoxyethylcarbonylphenylamino)-methylene-1,3-cyclohexadione;

5,5-diethyl-2-(4-ethoxyethylcarbonylphenylamino)-methylene-1,3-cyclohexadione;
5,5-diethyl-2-(4-methoxycarbomethyloxycarbonylphenylamino)-methylene-1,3-cyclohexadione;
5,5-diethyl-2-(4-ethoxycarbomethyloxycarbonylphenylamino)-methylene-1,3-cyclohexadione, and so on.

Of the aminomethylene derivatives represented by the general formula (I) used in the present invention, concrete examples of aminomethylene pyrone derivatives in which A in formula (I) is (b), represented by the formula (Ib):

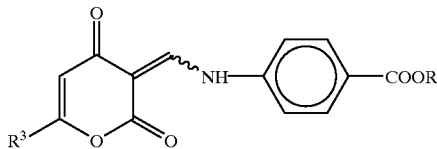

(Ib)

wherein $R^3$ and R are as defined above, include following compounds:
6-methyl-3-(4-ethoxycarbonylphenylaminomethylene)-2H,3H,4H-pyrane-2,4-dione;
6-methyl-3-(4-isopropoxycarbonylphenylaminomethylene)-2H,3H,4H-pyrane-2,4-dione;
6-methyl-3-(4-isobutoxycarbonylphenylaminomethylene)-2H,3H,4H-pyrane-2,4-dione;
6-methyl-3-(4-sec-butoxycarbonylphenylaminomethylene)-2H,3H,4H-pyrane-2,4-dione;
6-methyl-3-(4-tert-butoxycarbonylphenylaminomethylene)-2H,3H,4H-pyrane-2,4-dione;
6-methyl-3-(4-n-pentyloxycarbonylphenylaminomethylene)-2H,3H,4H-pyrane-2,4-dione;
6-methyl-3-(4-n-hexyloxycarbonylphenylaminomethylene)-2H,3H,4H-pyrane-2,4-dione;
6-methyl-3-(4-n-heptyloxycarbonylphenylaminomethylene)-2H,3H,4H-pyrane-2,4-dione;
6-methyl-3-(4-n-nonyloxycarbonylphenylaminomethylene)-2H,3H,4H-pyrane-2,4-dione;
6-methyl-3-(4-n-decyloxycarbonylphenylaminomethylene)-2H,3H,4H-pyrane-2,4-dione;
6-methyl-3-(4-n-undecyloxycarbonylphenylaminomethylene)-2H,3H,4H-pyrane-2,4-dione;
6-methyl-3-(4-n-dodecyloxycarbonylphenylaminomethylene)-2H,3H,4H-pyrane-2,4-dione;
6-methyl-3-(4-n-tridecyloxycarbonylphenylaminomethylene)-2H,3H,4H-pyrane-2,4-dione;
6-methyl-3-(4-n-tetradecyloxycarbonylphenylaminomethylene)-2H,3H,4H-pyrane-2,4-dione;
6-methyl-3-(4-n-pentadecyloxycarbonylphenylaminomethylene)-2H,3H,4H-pyrane-2,4-dione;
6-methyl-3-(4-n-hexadecyloxycarbonylphenylaminomethylene)-2H,3H,4H-pyrane-2,4-dione;
6-methyl-3-(4-n-heptadecyloxycarbonylphenylaminomethylene)-2H,3H,4H-pyrane-2,4-dione;
6-ethyl-3-(4-methoxycarbonylphenylaminomethylene)-2H,3H,4H-pyrane-2,4-dione;
6-ethyl-3-(4-ethoxycarbonylphenylaminomethylene)-2H,3H,4H-pyrane-2,4-dione;
6-ethyl-3-(4-n-propoxycarbonylphenylaminomethylene)-2H,3H,4H-pyrane-2,4-dione;
6-ethyl-3-(4-isopropoxycarbonylphenylaminomethylene)-2H,3H,4H-pyrane-2,4-dione;
6-ethyl-3-(4-n-butoxycarbonylphenylaminomethylene)-2H,3H,4H-pyrane-2,4-dione;
6-ethyl-3-(4-n-pentyloxycarbonylphenylaminomethylene)-2H,3H,4H-pyrane-2,4-dione;
6-ethyl-3-(4-n-hexyloxycarbonylphenylaminomethylene)-2H,3H,4H-pyrane-2,4-dione;
6-ethyl-3-(4-n-heptyloxycarbonylphenylaminomethylene)-2H,3H,4H-pyrane-2,4-dione;
6-ethyl-3-[4-(2-ethylhexyloxycarbonylphenyl)aminomethylene]-2H,3H,4H-pyrane-2,4-dione;
6-ethyl-3-(4-n-octadecyloxycarbonylphenylaminomethylene)-2H,3H,4H-pyrane-2,4-dione;
6-methyl-3-(4-methoxylethylcarbonylphenylaminomethylene)-2H,3H,4H-pyrane-2,4-dione;
6-methyl-3-(4-ethoxyethylcarbonylphenylaminomethylene)-2H,3H,4H-pyrane-2,4-dione;
5-methyl-3-(4-methoxycarbonylmethyloxycarbonylphenylaminomethylene)-2H,3H,4H-pyrane-2,4-dione;
6-methyl-3-(4-ethoxycarbonylmethyloxycarbonylphenylaminomethylene)-2H,3H,4H-pyrane-2,4-dione;
6-ethyl-3-(4-methoxyethylcarbonylphenylaminomethylene)-2H,3H,4H-pyrane-2,4-dione;
6-ethyl-3-(4-ethoxyethylcarbonylphenylaminomethylene)-2H,3H,4H-pyrane-2,4-dione;
6-ethyl-3-(4-methoxycarbonylmethyloxycarbonylphenylaminomethylene)-2H,3H,4H-pyrane-2,4-dione;
6-ethyl-3-(4-ethoxycarbonylmethyloxycarbonylphenylaminomethylene)-2H,3H,4H-pyrane-2,4-dione, and so on.

Of the aminomethylene derivatives represented by the general formula (I) used in the present invention, concrete examples of aminomethylene barbituric acid derivatives in which A in the formula (I) is (c), represented by the formula (Ic):

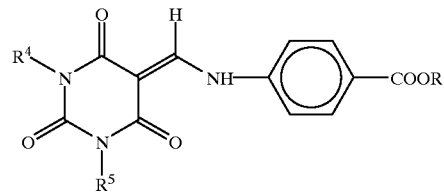

(Ic)

wherein $R^4$, $R^5$ and R are as defined above, include following compounds:
1,3-dimethyl-5-(4-ethoxycarbonylphenylamino)-methylene-barbituric acid;
1,3-dimethyl-5-(4-isopropoxycarbonylphenylamino)-methylene-barbituric acid;
1,3-dimethyl-5-(4-isobutoxycarbonylphenylamino)-methylene-barbituric acid;
1,3-dimethyl-5-(4-sec-butoxycarbonylphenylamino)-methylene-barbituric acid;
1,3-dimethyl-5-(4-tert-butoxycarbonylphenylamino)-methylene-barbituric acid;

1,3-dimethyl-5-(4-n-pentyloxycarbonylphenylamino)-methylene-barbituric acid;
1,3-dimethyl-5-(4-n-hexyloxycarbonylphenylamino)-methylene-barbituric acid;
1,3-dimethyl-5-(4-n-heptyloxycarbonylphenylamino)-methylene-barbituric acid;
1,3-dimethyl-5-(4-n-nonyloxycarbonylphenylamino)-methylene-barbituric acid;
1,3-dimethyl-5-(4-n-decyloxycarbonylphenylamino)-methylene-barbituric acid;
1,3-dimethyl-5-(4-n-undecyloxycarbonylphenylamino)-methylene-barbituric acid;
1,3-dimethyl-5-(4-n-dodecyloxycarbonylphenylamino)-methylene-barbituric acid;
1,3-dimethyl-5-(4-n-tridodecyloxycarbonylphenylamino)-methylene-barbituric acid;
1,3-dimethyl-5-(4-n-tetradodecyloxycarbonylphenylamino)-methylene-barbituric acid;
1,3-dimethyl-5-(4-n-pentadecyloxycarbonylphenylamino)-methylene-barbituric acid;
1,3-dimethyl-5-(4-n-hexadecyloxycarbonylphenylamino)-methylene-barbituric acid;
1,3-dimethyl-5-(4-n-heptadecyloxycarbonylphenylamino)-methylene-barbituric acid;
1,3-diethyl-5-(4-methoxycarbonylphenylamino)-methylene-barbituric acid;
1,3-diethyl-5-(4-ethoxycarbonylphenylamino)-methylene-barbituric acid;
1,3-diethyl-5-(4-n-propoxycarbonylphenylamino)-methylene-barbituric acid;
1,3-diethyl-5-(4-isopropoxycarbonylphenylamino)-methylene-barbituric acid;
1,3-diethyl-5-(4-n-butoxycarbonylphenylamino)-methylene-barbituric acid;
1,3-diethyl-5-(4-n-pentyloxycarbonylphenylamino)-methylene-barbituric acid;
1,3-diethyl-5-(4-n-hexyloxycarbonylphenylamino)-methylene-barbituric acid;
1,3-diethyl-5-(4-n-heptyloxycarbonylphenylamino)-methylene-barbituric acid;
1,3-diethyl-5-[4-(2-ethylhexyloxycarbonylphenylamino)]-methylene-barbituric acid;
1,3-diethyl-5-(4-n-octadecyloxycarbonylphenylamino)-methylene-barbituric acid;
1,3-dimethyl-5-(4-methoxyethylcarbonylphenylamino)-methylene-barbituric acid;
1,3-dimethyl-5-(4-ethoxyethylcarbonylphenylamino)-methylene-barbituric acid;
1,3-dimethyl-5-(4-methoxycarbomethyloxycarbonylphenylamino)-methylene-barbituric acid;
1,3-dimethyl-5-(4-ethoxycarbomethyloxycarbonylphenylamino)-methylene-barbituric acid;
1,3-diethyl-5-(4-methoxyethylcarbonylphenylamino)-methylene-barbituric acid;
1,3-diethyl-5-(4-ethoxyethylcarbonylphenylamino)-methylene-barbituric acid;
1,3-diethyl-5-(4-methoxycarbomethyloxycarbonylphenylamino)-methylene-barbituric acid;
1,3-diethyl-5-(4-ethoxycarbomethyloxycarbonylphenylamino)-methylene-barbituric acid, and so on.

Of the aminomethylene derivatives represented by the general formula (I) used in the present invention, concrete examples of aminomethylene chroman derivatives in which A in the formula (I) is (d), represented by the formula (Id):

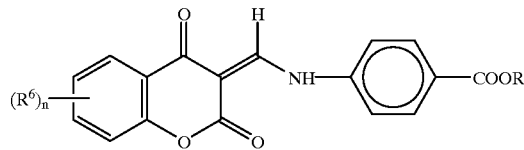

wherein $R^6$, n and R are as defined above, include following compounds:
3-(4-ethoxycarbonylphenylaminomethylene)chroman-2,4-dione;
3-(4-isopropoxycarbonylphenylaminomethylene)chroman-2,4-dione;
3-(4-isobutoxycarbonylphenylaminomethylene)chroman-2,4-dione;
3-(4-sec-butoxycarbonylphenylaminomethylene)chroman-2,4-dione;
3-(4-tert-butoxycarbonylphenylaminomethylene)chroman-2,4-dione;
3-(4-n-pentyloxycarbonylphenylaminomethylene)chroman-2,4-dione;
3-(4-n-hexyloxycarbonylphenylaminomethylene)chroman-2,4-dione;
3-(4-n-heptyloxycarbonylphenylaminomethylene)chroman-2,4-dione;
3-(4-n-nonyloxycarbonylphenylaminomethylene)chroman-2,4-dione;
3-(4-n-decyloxycarbonylphenylaminomethylene)chroman-2,4-dione;
3-(4-n-undecyloxycarbonylphenylaminomethylene)chroman-2,4-dione;
3-(4-n-dodecyloxycarbonylphenylaminomethylene)chroman-2,4-dione;
3-(4-n-tridecyloxycarbonylphenylaminomethylene)chroman-2,4-dione;
3-(4-n-tetradecyloxycarbonylphenylaminomethylene)chroman-2,4-dione;
3-(4-n-pentadecyloxycarbonylphenylaminomethylene)chroman-2,4-dione;
3-(4-n-hexadecyloxycarbonylphenylaminomethylene)chroman-2,4-dione;
3-(4-n-heptadecyloxycarbonylphenylaminomethylene)chroman-2,4-dione;
3-(4-methoxycarbonylphenylaminomethylene)chroman-2,4-dione;
3-(4-ethoxycarbonylphenylaminomethylene)chroman-2,4-dione;
3-(4-methoxyethylcarbonylphenylaminomethylene)chroman-2,4-dione;
3-(4-ethoxyethylcarbonylphenylaminomethylene)chroman-2,4-dione;
3-(4-methoxycarbonylmethyloxycarbonylphenylaminomethylene)-chroman-2,4-dione;
3-(4-ethoxycarbonylmethyloxycarbonylphenylaminomethylene)-chroman-2,4-dione;
3-(4-ethoxycarbonylmethyloxycarbonylphenylaminomethylene)-chroman-2,4-dione; and
5- or 6- or 7- or 8-methyl-3-(4-ethoxycarbonylphenylaminomethylene)chroman-2,4-dione;
5- or 6- or 7- or 8-methyl-3-(4-n-propoxycarbonylphenylaminomethylene)chroman-2,4-dione;
5- or 6- or 7- or 8-methyl-3-(4-n-butoxycarbonylphenylaminomethylene)chroman-2,4-dion;

5- or 6- or 7- or 8-ethyl-3-(4-methoxycarbonylphenylaminomethylene)chroman-2,4-dione;

5- or 6- or 7- or 8-ethyl-3-(4-ethoxycarbonylphenylaminomethylene)chroman-2,4-dione;

5- or 6- or 7- or 8-ethyl-3-(4-n-propoxycarbonylphenylaminomethylene)chroman-2,4-dione;

5- or 6- or 7- or 8-chloro-3-(4-ethoxycarbonylphenylaminomethylene)chroman-2,4-dione;

5- or 6- or 7- or 8-chloro-3-(4-n-propoxycarbonylphenylaminomethylene)chroman-2,4-dione;

5- or 6- or 7- or 8-chloro-3-(4-n-butoxycarbonylphenylaminomethylene)chroman-2,4-dione;

5- or 6- or 7- or 8-methoxy-3-(4-ethoxycarbonylphenylaminomethylene)chroman-2,4-dione;

5- or 6- or 7- or 8-methoxy-3-(4-n-propoxycarbonylphenylaminomethylene)chroman-2,4-dion;

5- or 6- or 7- or 8-methoxy-3-(4-n-butoxycarbonylphenylaminomethylene)chroman-2,4-dione;

5- or 6- or 7- or 8-acetyl-3-(4-methoxycarbonylphenylaminomethylene)chroman-2,4-dione;

5- or 6- or 7- or 8-acethyl-3-(4-ethoxycarbonylphenylaminomethylene)chroman-2,4-dione;

5- or 6- or 7- or 8-acetyl-3-(4-n-propoxycarbonylphenylaminomethylene)chroman-2,4-dione;

5- or 6- or 7- or 8-methylamino-3-(4-ethoxycarbonylphenylaminomethylene)chroman-2,4-dione;

5- or 6- or 7- or 8-methylamino-3-(4-n-propoxycarbonylphenylaminomethylene)chroman-2,4-dione;

5- or 6- or 7- or 8-methylamino-3-(4-n-butoxycarbonylphenylaminomethylene)chroman-2,4-dione;

5- or 6- or 7- or 8-acethylamino-3-(4-methoxycarbonylphenylaminomethylene)chroman-2,4-dione;

5- or 6- or 7- or 8-acethylamino-3-(4-ethoxycarbonylphenylaminomethylene)chroman-2,4-dione;

5- or 6- or 7- or 8-acethylamino-3-(4-n-propoxycarbonylphenylaminomethylene)chroman-2,4-dione;

5- or 6- or 7- or 8-dimethylamino-3-(4-ethoxycarbonylphenylaminomethylene)chroman-2,4-dione;

5- or 6- or 7- or 8-dimethylamino-3-(4-n-propoxycarbonylphenylaminomethylene)chroman-2,4-dione;

5- or 6- or 7- or 8-dimethylamino-3-(4-n-butoxycarbonylphenylaminomethylene)chroman-2,4-dione;

5- or 6- or 7- or 8-phenylamino-3-(4-methoxycarbonylphenylaminomethylene)chroman-2,4-dione;

5- or 6- or 7- or 8-phenylamino-3-(4-ethoxycarbonylphenylaminomethylene)chroman-2,4-dione;

5- or 6- or 7- or 8-phenylamino-3-(4-n-propoxycarbonylphenylaminomethylene)chroman-2,4-dione, and so on.

Of the aminomethylene derivatives represented by the general formula (I) used in the present invention, concrete examples of aminomethylene dioxane derivatives in which A in the formula (I) is (e), represented by the formula (Ie):

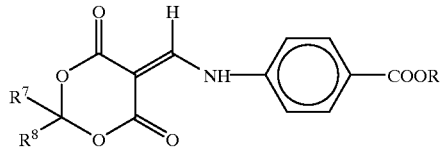

(Ie)

wherein $R^7$, $R^8$ and R are as defined above, include following compounds:

2,2-dimethyl-5-(ethoxycarbonylphenylaminomethylene)-1,3-dioxane-4,6-dione;

2,2-dimethyl-5-(4-isopropoxycarbonylphenylaminomethylene)-1,3-dioxane-4,6-dione;

2,2-dimethyl-5-(4-isobutoxycarbonylphenylaminomethylene)-1,3-dioxane-4,6-dione;

2,2-dimethyl-5-(4-sec-butoxycarbonylphenylaminomethylene)-1,3-dioxane-4,6-dione;

2,2-dimethyl-5-(4-tert-butoxycarbonylphenylaminomethylene)-1,3-dioxane-4,6-dione;

2,2-dimethyl-5-(4-n-pentyloxycarbonylphenylaminomethylene)-1,3-dioxane-4,6-dione;

2,2-dimethyl-5-(4-n-hexyloxycarbonylphenylaminomethylene)-1,3-dioxane-4,6-dione;

2,2-dimethyl-5-(4-n-heptyloxycarbonylphenylaminomethylene)-1,3-dioxane-4,6-dione;

2,2-dimethyl-5-(4-n-nonyloxycarbonylphenylaminomethylene)-1,3-dioxane-4,6-dione;

2,2-dimethyl-5-(4-n-decyloxycarbonylphenylaminomethylene)-1,3-dioxane-4,6-dione;

2,2-dimethyl-5-(4-n-undecyloxycarbonylphenylaminomethylene)-1,3-dioxane-4,6-dione;

2,2-dimethyl-5-(4-n-dodecyloxycarbonylphenylaminomethylene)-1,3-dioxane-4,6-dione;

2,2-dimethyl-5-(4-n-tridecyloxycarbonylphenylaminomethylene)-1,3-dioxane-4,6-dione;

2,2-dimethyl-5-(4-n-tetradecyloxycarbonylphenylaminomethylene)-1,3-dioxane-4,6-dione;

2,2-dimethyl-5-(4-n-pentadecyloxycarbonylphenylaminomethylene)-1,3-dioxane-4,6-dione;

2,2-dimethyl-5-(4-n-hexadecyloxycarbonylphenylaminomethylene)-1,3-dioxane-4,6-dione;

2,2-dimethyl-5-(4-n-heptadecyloxycarbonylphenylaminomethylene)-1,3-dioxane-4,6-dione;

2,2-diethyl-5-(4-methoxycarbonylphenylaminomethylene)-1,3-dioxane-4,6-dione;
2,2-diethyl-5-(4-ethoxycarbonylphenylaminomethylene)-1,3-dioxane-4,6-dione;
2,2-diethyl-5-(4-n-propoxycarbonylphenylaminomethylene)-1,3-dioxane-4,6-dione;
2,2-diethyl-5-(4-isopropoxycarbonylphenylaminomethylene)-1,3-dioxane-4,6-dione;
2,2-diethyl-5-(4-n-butoxycarbonylphenylaminomethylene)-1,3-dioxane-4,6-dione;
2,2-diethyl-5-(4-n-pentyloxycarbonylphenylaminomethylene)-1,3-dioxane-4,6-dione;
2,2-diethyl-5-(4-n-hexyloxycarbonylphenylaminomethylene)-1,3-dioxane-4,6-dione;
2,2-diethyl-5-(4-n-heptyloxycarbonylphenylaminomethylene)-1,3-dioxane-4,6-dione;
2,2-diethyl-5-[4-(2-ethylhexyloxycarbonylphenylaminomethylene)]-1,3-dioxane-4,6-dione;
2,2-diethyl-5-(4-n-octadecyloxycarbonylphenylaminomethylene)-1,3-dioxane-4,6-dione;
2,2-dimethyl-5-(4-methoxyethylcarbonylphenylaminomethylene)-1,3-dioxane-4,6-dione;
2,2-dimethyl-5-(4-ethoxyethylcarbonylphenylaminomethylene)-1,3-dioxane-4,6-dione;
2,2-dimethyl-5-(4-methoxycarbomethyloxycarbonylphenylaminomethylene)-1,3-dioxane-4,6-dione;
2,2-dimethyl-5-(4-ethoxycarbomethyloxycarbonylphenylaminomethylene)-1,3-dioxane-4,6-dione;
2,2-diethyl-5-(4-methoxyethylcarbonylphenylaminomethylene)-1,3-dioxane-4,6-dione;
2,2-diethyl-5-(4-ethoxyethylcarbonylphenylaminomethylene)-1,3-dioxane-4,6-dione;
2,2-diethyl-5-(4-methoxycarbomethyloxycarbonylphenylaminomethylene)-1,3-dioxane-4,6-dione;
2,2-diethyl-5-(4-ethoxycarbomethyloxycarbonylphenylaminomethylene)-1,3-dioxane-4,6-dione, and so on.

Of the starting materials employed in the manufacture of the compounds represented by the general formula (I), the compounds of formula (II) are concretely illustrated below.

The starting materials employed in the manufacture of the compounds of formula (Ia) are represented by the formula (IIa'):

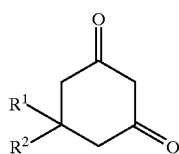

(IIa')

and include following compounds as concrete examples: 1,3-cyclohexanedione, 5,5-dimethyl-1,3-cyclohexanedione, 5,5-diethyl-1,3-cyclohexanedione, 5,5-di-n-propyl-1,3-cyclohexanedione, 5,5-di-isopropyl-1,3-cyclohexanedione, 5,5-di-n-butyl-1,3-cyclohexanedione, 5,5-di-isobutyl-1,3-cyclohexanedione, 5,5-di-sec-butyl-1,3-cyclohexanedione, 5,5-di-n-pentyl-1,3-cyclohexanedione, 5,5-di-n-hexyl-1,3-cyclohexanedione, 5,5-di-n-heptyl-1,3-cyclohexanedione, 5,5-di-n-octyl-1,3-cyclohexanedione, 5,5-diphenyl-1,3-cyclohexanedione, 5,5-dibenzyl-1,3-cyclohexanedione, 5,5-dicyclohexyl-1,3-cyclohexanedione, 5,5-di-o-tolyl-1,3-cyclohexanedione, 5,5-di-m-tolyl-1,3-cyclo-hexanedione, 5,5-di-p-tolyl-1,3-cyclohexanedione, 5,5-di-o-anisyl-1,3-cyclohexanedione, 5,5-di-m-anisyl-1,3-cyclohexanedione, 5,5-di-p-anisyl-1,3-cyclohexanedione, 5,5-di-o-chlorophenyl-1,3-cyclohexanedione, 5,5-di-m-chlorophenyl-1,3-cyclo-hexanedione, 5,5-di-p-chlorophenyl-1,3-cyclohexanedione, 5,5-di-o-bromophenyl-1,3-cyclohexanedione, 5,5-di-m-bromophenyl-1,3-cyclohexanedione, 5,5-di-p-bromophenyl-1,3-cyclohexanedione, 5,5-di-(2-methylcyclohexyl)-1,3-cyclohexanedione, 5,5-di-(3-methylcyclohexyl)-1,3-cyclohexanedione, 5,5-di-(4-methylcyclohexyl)-1,3-cyclohexanedione and so on.

The starting materials employed in the manufacture of the compounds of formula (Ib) are represented by the formula (IIb'):

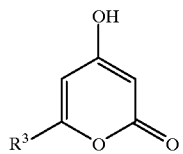

(IIb')

and include following compounds as concrete examples: 4-hydroxy-6-methyl-2-pyrone, 4-hydroxy-6-ethyl-2-pyrone, 4-hydroxy-6-n-propyl-2-pyrone, 4-hydroxy-6-isopropyl-2-pyrone, 4-hydroxy-6-n-butyl-2-pyrone, 4-hydroxy-6-isobutyl-2-pyrone, 4-hydroxy-6-sec-butyl-2-pyrone, 4-hydroxy-6-n-pentyl-2-pyrone, 4-hydroxy-6-n-hexyl-2-pyrone, 4-hydroxy-6-n-heptyl-2-pyrone, 4-hydroxy-6-n-octyl-2-pyrone, 4-hydroxy-6-(2-ethylhexyl)-2-pyrone, 4-hydroxy-6-cyclopentyl-2-pyrone, 4-hydroxy-6-cyclohexyl-2-pyrone, 4-hydroxy-6-allyl-2-pyrone, 4-hydroxy-6-benzyl-2-pyrone, 4-hydroxy-6-phenylethyl-2-pyrone, 4-hydroxy-6-phenyl-propyl-2-pyrone, 4-hydroxy-6-phenyl-2-pyrone, 4-hydroxy-6-o-tolyl-2-pyrone, 4-hydroxy-6-m-tolyl-2-pyrone, 4-hydroxy-6-p-tolyl-2-pyrone, 4-hydroxy-6-o-chlorophenyl-2-pyrone, 4-hydroxy-6-m-chlorophenyl-2-pyrone, 4-hydroxy-6-p-chlorophenyl-2-pyrone, 4-hydroxy-6-o-bromophenyl-2-pyrone, 4-hydroxy-6-m-bromophenyl-2-pyrone, 4-hydroxy-6-p-bromophenyl-2-pyrone, 4-hydroxy-6-o-anisyl-2-pyrone, 4-hydroxy-6-m-anisyl-2-pyrone, 4-hydroxy-6-p-anisyl-2-pyrone, 4-hydroxy-6-o-phenethyl-2-pyrone, 4-hydroxy-6-m-phenethyl-2-pyrone, 4-hydroxy-6-p-phenethyl-2-pyrone and so on.

The starting materials employed in the manufacture of the compounds of formula (Ic) are represented by the formula (IIc'):

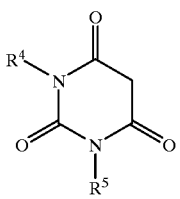

and include following compounds as concrete examples: barbituric acid, 1,3-dimethylbarbituric acid, 1,3-diethylbarbituric acid, 1,3-di-n-propylbarbituric acid, 1,3-di-iso-propylbarbituric acid, 1,3-di-n-butylbarbituric acid, 1,3-di-isobutylbarbituric acid, 1,3-di-sec-butylbarbituric acid, 1,3-di-n-pentylbarbituric acid, 1,3-di-n-hexylbarbituric acid, 1,3-di-n-heptylbarbituric acid, 1,3-di-n-octylbarbituric acid, 1,3-diphenylbarbituric acid, 1,3-dibenzylbarbituric acid, 1,3-dicyclohexylbarbituric acid, 1,3-di-o-tolylbarbituric acid, 1,3-di-m-tolylbarbituric acid, 1,3-di-p-tolylbarbituric acid, 1,3-di-o-anisylbarbituric acid, 1,3-di-m-anisylbarbituric acid, 1,3-di-p-anisylbarbituric acid, 1,3-di-o-chlorophenylbarbituric acid, 1,3-di-m-chlorophenylbarbituric acid, 1,3-di-p-chlorophenylbarbituric acid, 1,3-di-o-bromophenylbarbituric acid, 1,3-di-m-bromophenylbarbituric acid, 1,3-di-allylbarbituric acid, 1,3-di-(2-methylcyclohexyl)barbituric acid, 1,3-di-(3-methylcyclohexyl)barbituric acid, 1,3-di-(4-methylcyclohexyl)barbituric acid and so on.

The starting materials employed in the manufacture of the compounds of formula (Id) are represented by the formula (IId'):

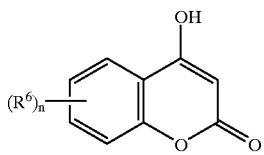

and include following compounds as concrete examples: 4-hydroxycoumarin, 4,5-dihydroxycoumarin, 4,6-dihydroxycoumarin, 4,7-dihydroxycoumarin, 4-hydroxy-5-methoxycoumarin, 4-hydroxy-6-methoxycoumarin, 4-hydroxy-7-methoxycoumarin, 4-hydroxy-5-methylcoumarin, 4-hydroxy-6-methylcoumarin, 4-hydroxy-7-methylcoumarin, 4-hydroxy-5-methoxycarbonylcoumarin, 4-hydroxy-6-methoxycarbonylcoumarin, 4-hydroxy-7-methoxycarbonylcoumarin, 4-hydroxy-5-ethoxycarbonylcoumarin, 4-hydroxy-6-ethoxycarbonylcoumarin, 4-hydroxy-7-ethoxycarbonylcoumarin, 4-hydroxy-5-acetylcoumarin, 4-hydroxy-6-acetylcoumarin, 4-hydroxy-7-acetylcoumarin, 4-hydroxy-5-aminocoumarin, 4-hydroxy-6-aminocoumarin, 4-hydroxy-7-aminocoumarin, 4-hydroxy-5-dimethylaminocoumarin, 4-hydroxy-6-dimethylaminocoumarin, 4-hydroxy-7-dimethylaminocoumarin, 4-hydroxy-5-diethylaminocoumarin, 4-hydroxy-6-diethylaminocoumarin, 4-hydroxy-7-diethylaminocoumarin, 4-hydroxy-5-di-n-propylaminocoumarin, 4-hydroxy-6-di-n-propylaminocoumarin, 4-hydroxy-7-di-n-propylaminocoumarin, 4-hydroxy-5-di-n-butylaminocoumarin, 4-hydroxy-6-di-n-butylaminocoumarin, 4-hydroxy-7-di-n-butylaminocoumarin, 4-hydroxy-5-methylaminocoumarin, 4-hydroxy-6-methylaminocoumarin, 4-hydroxy-7-methylaminocoumarin, 4-hydroxy-5-ethylaminocoumarin, 4-hydroxy-6-ethylaminocoumarin, 4-hydroxy-7-ethylaminocoumarin, 4-hydroxy-5-phenylaminocoumarin, 4-hydroxy-6-phenylaminocoumarin, 4-hydroxy-7-phenylaminocoumarin, 4-hydroxy-5-chlorocoumarin, 4-hydroxy-6-chlorocoumarin, 4-hydroxy-7-chlorocoumarin, 4-hydroxy-5-bromocoumarin, 4-hydroxy-6-bromocoumarin, 4-hydroxy-7-bromocoumarin and so on.

The starting materials employed in the manufacture of the compounds of formula (Ie) are represented by the formula (IIe'):

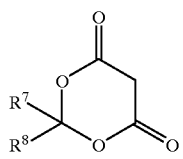

and include following compounds as concrete examples: 2,2-dimethy-1,3-dioxane-4,6-dione, 2,2-diethy-1,3-dioxane-4,6-dione, 2,2-di-n-propyl-1,3-dioxane-4,6-dione, 2,2-di-isopropyl-1,3-dioxane-4,6-dione, 2,2-di-n-butyl-1,3-dioxane-4,6-dione, 2,2-di-isobutyl-1,3-dioxane-4,6-dione, 2,2-di-sec-butyl-1,3-dioxane-4,6-dione, 2,2-di-n-pentyl-1,3-dioxane-4,6-dione, 2,2-di-n-hexyl-1,3-dioxane-4,6-dione, 2,2-di-n-heptyl-1,3-dioxane-4,6-dione, 2,2-di-n-octyl-1,3-dioxane-4,6-dione, 2,2-di-(2-ethylhexyl)-1,3-dioxane-4,6-dione, 2,2-dicyclopentyl-1,3-dioxane-4,6-dione, 2,2-dicyclohexyl-1,3-dioxane-4,6-dione, 2,2-diphenyl-1,3-dioxane-4,6-dione, 2,2-dibenzyl-1,3-dioxane-4,6-dione, 2,2-diphenylethyl-1,3-dioxane-4,6-dione, 2,2-diphenylpropyl-1,3-dioxane-4,6-dione, 2,2-di-o-anisyl-1,3-dioxane-4,6-dione, 2,2-di-m-anisyl-1,3-dioxane-4,6-dione, 2,2-di-p-anisyl-1,3-dioxane-4,6-dione, 2,2-di-o-phenethyl-1,3-dioxane-4,6-dione, 2,2-di-m-phenethyl-1,3-dioxane-4,6-dione, 2,2-di-p-phenethyl-1,3-dioxane-4,6-dione, 2,2-di-o-chlorophenyl-1,3-dioxane-4,6-dione, 2,2-di-m-chlorophenyl-1,3-dioxane-4,6-dione, 2,2-di-p-chlorophenyl-1,3-dioxane-4,6-dione, 2,2-di-o-bromophenyl-1,3-dioxane-4,6-dione, 2,2-di-m-bromophenyl-1,3-dioxane-4,6-dione, 2,2-di-p-bromophenyl-1,3-dioxane-4,6-dione, 2,2-di-o-tolyl-1,3-dioxane-4,6-dione, 2,2-di-m-tolyl-1,3-dioxane-4,6-dione, 2,2-di-p-tolyl-1,3-dioxane-4,6-dione and so on.

The compounds of formula (III) described above which are another starting materials employed in the manufacture of the compounds of formula (I), include following compounds as concrete examples: methyl N-formylaminobenzoate, ethyl N-formylaminobenzoate, n-propyl N-formylaminobenzoate, isopropyl N-formylaminobenzoate, n-butyl N-formylaminobenzoate, isobutyl N-formylaminobenzoate, sec-butyl N-formylaminobenzoate, tert-butyl N-formylaminobenzoate, n-pentyl N-formylaminobenzoate, n-hexyl N-formylaminobenzoate, n-heptyl N-formylaminobenzoate, n-octyl N-formylaminobenzoate, 2-ethylhexyl N-formylaminobenzoate, n-nonyl N-formylaminobenzoate, n-nonyl N-formylaminobenzoate, n-decyl N-formylaminobenzoate, n-undecyl N-formylaminobenzoate, n-dodecyl N-formylaminobenzoate, n-tetradecyl N-formylaminobenzoate, n-pentadecyl N-formylaminobenzoate, n-hexadecyl N-formylaminobenzoate, n-heptadecyl N-formylaminobenzoate, n-octadecyl N-formylaminobenzoate, n-nanodecyl N-formylaminobenzoate, benzyl N-formylaminobenzoate, phenethyl N-formylaminobenzoate, phenyl-propyl N-formylaminobenzoate, phenyl N-formylaminobenzoate, o-anisyl N-formylaminobenzoate, m-anisyl N-formylaminobenzoate, p-anisyl N-formylaminobenzoate, o-tolyl N-formylaminobenzoate, m-tolyl N-formylaminobenzoate, p-tolyl N-formylaminobenzoate, o-phenethyl N-formylaminobenzoate, m-phenethyl N-formylaminobenzoate, p-phenethyl N-formylaminobenzoate, cyclopentyl N-formylaminobenzoate, cyclohexyl N-formylaminobenzoate, methoxyethyl N-formylaminobenzoate, ethoxyethyl N-formylaminobenzoate, methoxycarbonylmethyl N-formylaminobenzoate, ethoxycarbonylmethyl N-formylaminobenzoate and so on.

Examples of antioxidants which can be added in addition to compounds according to the present invention include following compounds:

2,6-di-tert-butyl-4-methylphenol;
2-tert-butyl-4,6-dimethylphenol;
2,6-di-tert-butyl-4-ethylphenol;
2,6-di-tert-butyl-4-n-butylphenol;
2,6-di-tert-butyl-4-isobutylphenol;
2,6-di-cyclopentyl-4-methylphenol;
2-(α-methylcyclohexyl)-4,6-dimethylphenol;
2,6-dioctadecyl-4-methylphenol;
2,4,6-tricyclohexylphenol;
2,6-dinonyl-4-methyphenol;
2,6-di-tert-butyl-4-methoxymethylphenol;
2,4-dimethyl-6-(1'-methyl-undeca-1'-yl)-phenol;
2,4-dimethyl-6-(1'-methyl-heptadeca-1'-yl)-phenol;
2,4-dimethyl-6-(1'-methyl-trideca-1'-yl)-phenol and mixture thereof;
2,4-di-octylthiomethyl-6-tert-butylphenol;
2,4-di-octylthiomethy-6-methylphenol;
2,4-di-octylthiomethy-6-ethylphenol;
2,6-di-dodecylthiomethyl-4-nonylphenol and mixutre thereof;
2,6-di-tert-butyl-4-methoxyphenol;
2,5-di-tert-butylhydroquinone;
2,5-di-tert-amylhydroquinone;
2,6-diphenyl-4-octadecyloxyphenol;
2,6-di-tert-butylhydroquinone;
2,5-di-tert-butyl-4-hydroxyanisole;
3,5-di-tert-butyl-4-hydroxyanisole;
3,5-di-tert-butyl-4-hydroxyphenylstearate;
bis(3,5-di-tert-butyl-4-hydroxyphenyl)adipate and mixture thereof;
2,4-bis-octylmercapt-6-(3,5-di-tert-butyl-4-hydroxyanilino)-1,3,5-trizine;
2-octylmercapto-4,6-bis(3,5-di-tert-butyl-4-hydroxyanilino)-1,3,5-trizine;
2-octylmercapto-4,6-bis(3,5-di-tert-butyl-4-hydroxyphenoxy)-1,3,5-triazine;
2,4,6-tris(3,5-di-tert-butyl-4-hydroxyphenoxy)-1,2,3-triazine;
1,3,5-tris(3,5-di-tert-butyl-4-hydroxybenzyl)-isocyanurate;
1,3,5-tris(4-tert-butyl-3-hydroxy-2,6-dimethylbenzyl)-isocyanurate;
2,4,6-tris(3,5-di-tert-butyl-4-hydroxyphenylethyl)-1,3,5-triazine;
1,3,5-tris(3,5-di-tert-butyl-4-hydroxyphenylpropionyl)-hexahydro-1,3,5-triazine;
1,3,5-tris(3,5-dicyclohexyl-4-hydroxybenzyl)-isocyanurate or the like; and
2,2'-methylenebis(6-tert-butyl-4-methylphenol);
2,2'-methylenebis(6-tert-butyl-4-ethylphenol);
2,2'-ethylidenebis(4,6-di-tert-butylphenol);
2,2'-ethylidenebis(6-tert-butyl-4-isobutylphenol);
4,4'-methylenebis(2,6-di-tert-butylphenol);
4,4'-methylenebis(6-tert-butyl-2-methylphenol); 1,1-bis(5-tert-butyl-4-hydroxy-2-methylphenyl)butane;
ethylene glycol bis[3,3'-bis(3'-tert-butyl-4'-hydroxyphenyl)butylate]or the like; and
1,3,5-tris(3,5-di-tert-butyl-4-hydroxybenzyl)-2,4,6-trimethylbenzene;
1,4-bis(3,5-di-tert-butyl-4-hydroxybenzyl)-2,3,5,6-tetramethylbenzene;
2,4,6-tris(3,5-di-tert-butyl-4-hydroxybenzyl)phenol or the like.

Examples of light stabilizing agents which can be added in addition to compounds according to the present invention include following compounds:

2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-[2'-hydroxy-5'-(1,1,3,3-tetra-methylbutyl)phenyl]benzotriazole, 2-(3',5'-di-tert-butyl-2'-hydroxyphenyl)-5-chlorobenzotriazole, 2-(3'-tert-butyl-2'-hydroxy-5'-methyphenyl)-5-chlorobenzotriazole, 2-(2'-hydroxy-4'-octoxyphenyl) benzotriazole, 2-(3',5'-di-tert-amyl-2'-hydroxyphenyl) benzotriazole, 2-[3'-tert-butyl-2'-hydroxy-5'-(2'-octyloxycarbonylethylphenyl)-5-chlorobenzotriazole or the like;

4-hydroxy-, 4-methoxy-, 4-octoxy-, 4-decyloxy-, 4-dodecyloxy-, 4-benzyloxy-, 4,2',4'-trihydroxy-, 2'-hydroxy-4,4'-dimethoxy- or 4-(2-ethylhexyloxy)-2-hydroxybenzophenone derivatives or the like;

4-tert-butylphenyl salicylate, phenyl salicylate, octylphenyl salicylate, dibenzoyl resorcinol, bis(4-tert-butylbenzoyl resorcinol, 2,4-di-tert-butylphenyl 3,5-di-tert-butyl-4-hydroxybenzoate, hexadecyl 3,5-di-tert-butyl-4-hydroxybenzoate or the like; ethyl α-cyano-β,β-diphenylacrylate, isooctyl α-cyano-β,β-diphenylacrylate, methyl α-carbomethoxycinnamate, methyl α-cyano-β-methyl-p-methoxycinnamate or the like; bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)adipate or the like;

4,4'-di-octyloxyoxanilide, 2,2'-diethoxyoxyoxanilide, 2,2'-di-octyloxy-5,5'-di-tert-butyloxanilide, 2,2'-di-dodecyloxy-5,5'-di-tert-butyloxanilide, 2-ethoxy-2'-ethyloxanilide, N,N'-bis-(3-dimethylaminopropyl) oxanilide, 2-ethoxy-5-tert-butyl-2'-ethoxyoxanilide or the like;

2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethyl-phenyl)-1,3,5-triazine, 2,4-bis(2-hydroxy-4-propyloxyphenyl)-6-(2,4-dimethylphenyl)-1,3,5-triazine, 2-(2-hydroxy-4-dodecyloxy-phenyl)-4,6-bis(2,4-dimethylphenyl)-1,3,5-triazine or the like.

Example of metal inactivators which can be added in addition to compounds according to the present invention include, N,N'-diphenyloxamide, N-salcylal-N'-salicyloyl-hydrazine, N,N'-bis(salicyloyl)hydrazine, N,N'-bis(3,5-ditert-butyl-4-hydroxyphenylpropionyl)hydrazine, 3-salicylolyamino-1,2,3-triazole, bis(benzylidene)oxalic acid hydrazide, isophthalic acid dihydrazide, N,N'-diacetaladipic acid dihydrazide, N,N'-bis-salicyloyloxalic acid dihydrazide, N,N'-bis(salicyloyl)thiopropionic acid dihidrazide or the like.

Examples of peroxide scavengers which can be added in addition to compounds according to the present invention include, dilauryl thiodipropionate, distearyl thiodipropionate, dimyristyl thiodipropionate or ditridecyl thiodipropionate, 2-mercaptobenzimidazole, pentaerythritoltetrakis(dodecyl-mercapto)propionate or the like.

The aminomethylene derivatives of the present invention have preferred chracteriscits, that they have much higher ultraviolet absorption compared to that of conventionally known ultraviolet absorbent for UV-A range, as the maximum absorption range of aminomethylene cyclohexane derivatives of the present invention represented by the general formula (I) in which A is (a) is 340 to 360 nm, the maximum absorption range of aminomethylene pyrone derivatives of the present invention represented by the general formula (I) in which A is (b) is 340 to 360 nm, and the maximum absorption range of aminomethylene barbituric acid derivatives of the present invention represented by the general formula (I) in which A is (c) is 340 to 360 nm, the maximum absorption range of aminomethylene chroman derivatives of the present invention represented by the general formula (I) in which A is (d) is 340 to 380 nm, and the maximum absorption range of aminomethylene dioxane derivatives of the present invention represented by the general formula (I) in which A is (e) is 330 to 350 nm, and the present compounds have lower irritability and no other toxicity, higher compatibility to other cosmetic bases, and smaller percutaneous absorption.

The base for skin ointment which is also the cosmetic materials according to the present invention can be any that is inactive to above described aminomethylene derivatives (I), and can be solid, liquid, emulsion, foaming solution, gel or the like. Examples of the cosmetic base of the present invention include olive oil, tsubaki oil, cotton seed oil, castor oil, soybean oil, coconut oil, cacao butter, lanoline, bees wax, carnauba wax, hardened oil, stearic acid, palmitic acid, myristic acid, ascorbic acid, behenic acid, and esters or metal salts thereof, higher alcohol including decylethyl, oleyl, lauryl, cetyl or stearyl alcohol. Examples of other base include synthetic oil such as squalene monostearic acid glyceride, synthetic polyether oils, sorbitan monooleate, lanoline and hydrogenated forms thereof and squalenes; mineral oil such as paraffin, petrolatum, liquid paraffin, microcrystal wax or the like. Further, other examples of base which can be used include silicone oil, polyethers, dialkylsiloxanes, fine powders of starch or talc, carbohydrate with lower boiling point or carbohydrate containing halogen both of which are used as a switchsbout type power propellant.

Examples of the humectants include glycerin, propylene glycol, sorbitol, polyethylene glycol, sodium pyrrolidone carboxylate or the like. Examples of sticking agents include polyvinyl alcohol, sodium salt of carboxymethyl cellulose, sodium alginate, propylene glycol ester or the like.

Examples of the preservatives include benzoic acid, sorbic acid, dehydroacetic acid, p-hydroxy benzoic acid esters or the like. Examples of the solvent include ethanol, acetone, acetates, isopropanol or the like.

Examples of ultraviolet absorbent which can be combinedly used include benzotriazoles such as 2-(2'-hydroxy-5'-methylphenyl)benzotriazole, 2-(2'-hydroxy-3'-tert-butyl-5'-methylphenyl)-5-chlorobenzotriazole, 2-(2'-hydroxy-3', 5'-di-tert-butylphenyl)-5-chlorobenzotriazole, 2-(2'-hydroxy-3',5'-di-tert-butylphenyl)benzotriazole, 2-(2'-hydroxy-4'-n-octoxyphenyl)-benzotriazole or the like;

benzophenones such as 2-hydroxy-4-methoxy-2'-carboxybenzophenone, 2-hydroxy-4-methoxybenzophenone, 2-hydroxy-4-n-octoxybenzophenone, 2,2'-dihydroxy-4,4'-dimethoxybenzophenone, 2,2'-dihydroxy-4,4'-dimethoxy-5-sulfobenzophenone, 2-hydroxy-4-methoxybenzophenone-5-sulfonic acid, 2-hydroxy-4-octadecyloxybenzophenone, 2,2',4,4'-tetrahydroxybenzophenone, 2-hydroxy-4-dodecyloxybenzophenone, 2-hydroxy-4-(2-hydroxy-3-methacryloxy)propoxybenzophenone or the like;

compounds belonging to benzoic acid family such as methyl o-benzoyl benzoate, p-aminobenzoic acid, glyceryl p-aminobenzoate, ethyl p-aminobenzoate, 2-ethylhexyl p-dimethylaminobenzoate, octyl p-dimethylaminobenzoate, ethyl 4-bis(hydroxybutyl) aminobenzoate, methyl o-aminobenzoate or the like;

compounds belonging to cinnamic acid family such as benzyl cinnamate, p-methoxycinnamic acid diethanolamine, 2-ethylhexyl p-methoxycinnamate, isopropyl p-methoxycinnamate or the like; and other acid esters such as gallic acid triesters, 2-ethylhexyl salicylate, 3,3,5-trimethylcyclohexyl salicylate, salicylic acid triethanolamine, p-butylphenyl salicylate, 2-ethylhexyl 2-cyano-3,3-diphenylacrylate, 2-ethylhexyl 3-cyano-3,3-diphenylacrylate or the like.

Cosmetic materials containing above described aminomethylene derivatives (I) of the present invention are produced by adding the same to above described known cosmetic base using an ordinary method to prepare cream, solution, oil, spray, stick, emulsion, foundation, and ointment.

Formulation ratio of above described aminomethylene derivatives (I) in the cosmetic materials of the present invention can differ according to the form of use and is not limited, and can be any amount that is effective, and in general the aminomethylene derivatives is added to the composition at a ratio of 0.1 to 20 weight %, preferably 0.5 to 5 weight %. Further above described aminomethylene derivatives (I) of the present invention can be added alone but more preferable effect can be obtained by combining with other UV-B absorbents, UV-A absorbents or the like, when it is used for ordinary sunscreen cosmetics. Above described aminomethylene derivatives (I) of the present invention can be used by combining with many other additives. Examples of suitable additives include emulsion of W/O type and O/W type. Regarding emulsifiers, commercially available emulsifiers including polyglycerin fatty acid esters, polyoxyethylene lanolin derivatives, polyoxyethylene sorbitan fatty acid esters, polyoxyethylene polyoxypropylene alkylethers, polyoxyethylene-sorbitol fatty acid esters, sucrose fatty acid esters, propylene glycol fatty acid esters or the like. Further, thickeners including ethylcellulose, polyacrylic acid, gelatin, agar or the like can be added if necessary. In addition, perfumes, humectants, emulsifying agents, medically active ingredients and others may be optionally added.

EXAMPLES

The present invention will be further described with reference to the following examples of synthesis of the compounds of the invention, and cosmetic materials and polymer composition comprising said compounds, however these examples are intended to show some preferred embodiments and are not to be constructed to limit the scope of the invention.

Example 1

Synthesis of 2-(4-methoxycarbonylphenylamino)-methylene-1,3-cyclohexadione [compound represented by the general formula (I) of which A is (a), $R^1=R^2$=hydrogen atom and R=methyl]

After stirring suspension containing 0.20 mol of 1,3-cyclohexanedione, 0.50 mol of 4-methoxycarbonyl-N-formanilide and 25 ml of toluene, 0.50 mol of phosphorus oxychloride is added to the suspension over 15 minutes. During the addition, temperature is maintained at 45° C. or lower. The suspension is further stirred for 10 minutes, then 250 ml of hot solution of toluene containing 0.48 mol of 1,3-cyclohexanedione is added to at 60 to 65° C., over 45 minutes. The reaction mixture is constantly stirred and allowed to cool to room temperature, and reaction is terminated by adding the reaction mixture dropwise into 600 ml of 15% sodium hydroxide solution. Obtained organic layer is being washed with 200 ml of saturated aqueous solution of sodium chloride. The organic layer is fractionated, allowed to dry on anhydrous sodium sulfate, filtrated and concentrated to obtaine crude product.

Purified product having the melting point of 198 to 199° C. is obtained through recrystalization from ethanol.

Mass spectrum: m/z 274(M++1, 17%), 273(M+, 96), 242(16), 217(58), 202(24), 144(25), 123(19), 89(10);

Ultraviolet absorption spectrum (ethanol): λ max(nm) 358 (ε max 38,000).

Example 2

Synthesis of 2-(4-n-propoxycarbonylphenylamino)-methylene-1,3-cyclohexadione [compound represented by the general formula (I) of which A is (a), $R^1=R^2$=hydrogen atom and R=n-propyl]

Title compound was synthesized from 1,3-cyclohexanedione and 4-n-propyloxycarbonyl-N-formanilide using the same reaction conditions and after-treatment used in EXAMPLE 1.

Purified product having the melting point of 147.5 to 148.5° C. was obtained through recrystalization from ethanol.

Mass spectrum: m/z 302(M++1, 25%), 301(M+, 100), 259(18), 245(52), 242(37), 230(18), 203(12), 188(10), 144 (26), 123(22), 89(10);

Ultraviolet absorption spectrum (ethanol): λ max(nm) 358 (ε max 34,000).

Example 3

Synthesis of 2-(4-n-butoxycarbonylphenylamino)-methylene-1,3-cyclohexadione [compound represented by the general formula (I) of which A is (a), $R^1=R^2$=hydrogen atom and R=n-butyl]

Title compound was synthesized from 1,3-cyclohexanedione and 4-n-butyloxycarbonyl-N-formanilide using the same reaction conditions and after-treatment used in EXAMPLE 1.

Purified product having the melting point of 144.5 to 146° C. was obtained through recrystalization from ethanol.

Mass spectrum: m/z 316(M++1, 20%), 315(M+, 100), 260(12), 259(70), 242(32), 203(13), 144(15), 123(13);

Ultraviolet absorption spectrum (ethanol): λ max(nm) 358 (ε max 33,800).

Example 4

Synthesis of 2-(4-n-octadecyloxycarbonylphenylamino)-methylene-1,3-cyclohexadione [compound represented by the general formula (I) of which A is (a), $R^1=R^2$=hydrogen atom and R=n-octadecyl]

Title compound was synthesized from 1,3-cyclohexanedione and 4-n-octadecyloxycarbonyl-N-formanilide using the same reaction conditions and after-treatment used in EXAMPLE 1.

Purified product having the melting point of 114.5 to 115.5° C. was obtained through recrystalization from ethanol.

Mass spectrum: m/z 512(M++1, 17%), 511(M+, 48), 389(22), 260(14), 242(11), 215(12), 138(26), 137(100), 120 (31);

Ultraviolet absorption spectrum (ethanol): λ max(nm) 363 (ε max 27,000).

Example 5

Synthesis of 5,5-dimethyl-2-(4-methoxycarbonylphenylamino)-methylene-1,3-cyclohexadione [compound represented by the general formula (I) of which A is (a), $R^1=R^2$=methyl and R=methyl]

Title compound was synthesized from dimedone and 4-methoxycarbonyl-N-formanilide using the same reaction conditions and after-treatment used in EXAMPLE 1.

Purified product having the melting point of 193 to 194.5° C. was obtained through recrystalization from ethanol.

Mass spectrum: m/z 302(M++1, 20%), 301(M+, 100), 270(12), 217(65), 202(16), 151(10), 144(19);

Ultraviolet absorption spectrum (ethanol): λ max(nm) 358 (ε max 50,000).

Example 6

Synthesis of 5,5-dimethyl-2-(4-n-propoxycarbonylphenylamino)-methylene-1,3-cyclohexadione [compound represented by the general formula (I) of which A is (a), $R^1=R^2$=methyl and R=n-propyl]

Title compound was synthesized from dimedone and 4-n-propyloxycarbonyl-N-formanilide using the same reaction conditions and after-treatment used in EXAMPLE 1.

Purified product having the melting point of 182 to 183° C. was obtained through recrystalization from ethanol.

Mass spectrum: m/z 330(M++1, 21%), 329(M+, 100), 270(21), 245(43), 144(13);

Ultraviolet absorption spectrum (ethanol): λ max(nm) 358 (ε max 49,000).

Example 7

Synthesis of 5,5-dimethyl-2-(4-n-butoxycarbonylphenylamino)-methylene-1,3-cyclohexadione [compound represented by the general formula (I) of which A is (a), $R^1=R^2$=methyl and R=n-butyl]

Title compound was synthesized from dimedone and 4-n-butyloxycarbonyl-N-formanilide using the same reaction conditions and after-treatment used in EXAMPLE 1.

Purified product having the melting point of 169.5 to 170° C. was obtained through recrystalization from ethanol.

Mass spectrum: m/z 344(M++1, 23%), 343(M+, 100), 287(32), 270(23), 259(34), 203(12), 144(13);

Ultraviolet absorption spectrum (ethanol): λ max(nm) 358 (εmax 48,700).

Example 8

Synthesis of 5,5-dimethyl-2-[4-(2-ethylhexyloxycarbonylphenylamino)]-methylene-1,3-cyclohexadione [compound represented by the general formula (I) of which A is (a), $R^1=R^2$=methyl and R=2-ethylhexyl]

Title compound was synthesized from dimedone and 4-(2-ethylhexyloxycarbonyl)-N-formanilide using the same reaction conditions and after-treatment used in EXAMPLE 1.

Purified product having the melting point of 123.5 to 124.5° C. was obtained through recrystalization from ethanol.

Mass spectrum: m/z 400(M++1, 8%), 399(M+, 39), 288 (22), 287(100), 270(26), 203(27);

Ultraviolet absorption spectrum (chloroform): λ max(nm) 364 (ε max 53,600).

Example 9

Synthesis of 5,5-dimethyl-2-(4-n-octadecyloxycarbonylphenylamino)-methylene-1,3-cyclohexadione [compound represented by the general formula (I) of which A is (a), $R^1=R^2$=methyl and R=n-octadecyl]

Title compound was synthesized from dimedone and 4-n-octadecyloxycarbonyl-N-formanilide using the same reaction conditions and after-treatment used in EXAMPLE 1.

Purified product having the melting point of 115 to 116.5° C. was obtained through recrystalization from ethanol.

Mass spectrum: m/z 540(M++1, 39%), 539(M+, 100), 525(12), 524(32), 288(28), 271(15), 270(25), 243(36), 137 (17), 120(19);

Ultraviolet absorption spectrum (chloroform): λ max(nm) 363 (ε max 40,000).

Example 10

Practical examples of formulation of skin ointment according to the present invention hereunder will be described.

According to the formulation listed in Table 1, a cosmetic liquid containing the compound according to EXAMPLE 8, that is 5,5-dimethyl-2-[4-(2-ethylhexyloxycarbonylphenylamino)]-methylene-1,3-cyclohexadione and as control cosmetic liquids, cosmetic liquids containing compound of Control 1, that is 2,2',4,4'-tetrahydroxybenzophenone, and compound of Control 2, that is 2-ethylhexyl p-methoxycinnamate, respectively, were prepared.

TABLE 1

| Composition | EXAMPLE 10 | Control 1 | Control 2 |
| --- | --- | --- | --- |
| ethanol | 8.0 | 8.0 | 8.0 |
| glycerin | 2.0 | 2.0 | 2.0 |
| citric acid | 0.02 | 0.02 | 0.02 |
| sodium citrate | 0.1 | 0.1 | 0.1 |
| methylparaben | 0.05 | 0.05 | 0.05 |
| POE hardened castor oil | 0.5 | 0.5 | 0.5 |
| perfume | some | some | some |

TABLE 1-continued

| Composition | EXAMPLE 10 | Control 1 | Control 2 |
| --- | --- | --- | --- |
| compound of EXAMPLE 8 | 1.0 | — | — |
| compound of Control 1 | — | 1.0 | — |
| compound of Control 2 | — | — | 1.0 |
| propylene glycol | 7.0 | 7.0 | 7.0 |
| purified water | rest | rest | rest |

Control 1 exhibited pale yellow and was not suitable for cosmetic liquid.

Confirmation of Sunscreening Effect

Cosmetic liquid according to EXAMPLE 10 in which compound produced according to EXAMPLE 8 and that of Control 2 were, respectively, applied on the skin and their effect at practical use in beach was tested. On each of right or left half area of the back of ten respective male and female, each sample solution was applied, and the degree of suntan was examined and obtained results was listed in Table 2. According to the degree of suntan, results were estimated based on the following estimation criteria.

| Estimation Criteria | |
| --- | --- |
| no rash | ○ |
| slight rash | Δ |
| severe rash | × |

TABLE 2

| Estimation criteria | Area applied with EXAMPLE 10 | Area applied with Control 2 |
| --- | --- | --- |
| ○ | 17 | 12 |
| Δ | 3 | 6 |
| Δ – × | 0 | 2 |
| × | 0 | 0 |
| Frequency of skin trouble | No | itching 7 cases slight rash 1 case |

Example 11

Light Stability Effect for Polymer Materials

Each of 0.05, 0.2 and 0.5 part by weight of sample produced according to EXAMPLE 8 was formulated with 100 parts by weight of polyethylene powder or polypropylene powder, mixed well using a mixer, then melted and kneaded using a extruder having the diameter of 25 mm at cylinder temperature of 200° C., and pelletized. Obtained pellets were compacted into sheets of 0.25 mm thickness at 210° C. to prepare test strips. Obtained test strips were punched into dumbbell shapes accommodating to a tension test. Test strip of control which did not contain light stabilizing agent was prepared, using the above described same method, and test strips were examined.

Using the WEL-75XS-HS-BEC model xenon sunshine long-life weatherometer manufactured by Suga Shiken-Kiki Co. Ltd., these test strips were light-irradiated with black panel temperature of 80° C., and were examined for lowering in tensile strength over time.

The tension test was performed at 23±2° C., relative humidity of 50±5%, test speed of 50±5.0 mm/minutes, using the DSS-5000 model tension meter manufactured Shimadzu Seisakusho Co. Ltd. Tension strength was calculated according to the following method.

Equation 1

Ts=S/T·W wherein,
Ts=tension strength (kgf/mm$^2$)
T=thickness of samples (mm)
W=wide of samples (mm)
S=maximum strength of samples (kgf)

Obtained results were as listed by Table 3. As apparent from the results shown in Table 3, the aminomethylene cyclohexane derivatives according to the present invention show prominent stabilizing effect (that is, elongated time to deterioration).

TABLE 3

|  | (unit: kgf) | | | | | |
| --- | --- | --- | --- | --- | --- | --- |
| Name of resin | 200 hrs | 400 hrs | 600 hrs | 800 hrs | 1000 hrs | 1200 hrs |
| Polypropylene: no, | 3.15 | 2.13 | 0 | — | — | — |
| 0.05 (wt%) | 3.60 | 3.10 | 2.90 | — | — | — |
| 0.2 (wt%) | 3.70 | 3.45 | 3.40 | — | — | — |
| 0.5 (wt%) | 3.98 | 3.80 | 3.65 | — | — | — |
| Polyethylene: no, | 2.42 | 2.29 | 2.25 | 2.10 | 1.90 | 0 |
| 0.05 (wt%) | 2.65 | 2.56 | 2.50 | 2.45 | 2.30 | 2.21 |
| 0.2 (wt%) | 2.81 | 2.70 | 2.62 | 2.55 | 2.42 | 2.39 |
| 0.5 (wt%) | 2.88 | 2.80 | 2.75 | 2.70 | 2.63 | 2.60 |

Example 12

Synthesis of 6-methyl-3-(4-methoxycarbonylphenyaminomethylene)-2H,3H,4H-pyran-2,4-dione [compound represented by general (I) in which A is (b) and R$^3$=methyl, R=methyl]

Suspension containing 0.20 mol of 4-hydroxy-6-methyl-2-pyrone, 0.50 mol of 4-methoxycarbonyl-N-formanilide and 25 ml of toluene was mixed and added with 0.50 mol of phosphorous oxychloride over 15 minutes. During the addition temperature was maintained at 45° C. or lower. The suspension is further stirred for 10 minutes, then 250 ml of hot solution of toluene containing 0.48 mol of 4-hydroxy-6-methyl-2-pyrone is added to at 60 to 65° C., over 45 minutes. The reaction mixture is constantly stirred and allowed to cool to room temperature, and reaction is terminated by adding the reaction mixture dropwise into 600 ml of 15% sodium hydroxide solution. Obtained organic layer is being washed with 200 ml of saturated aqueous solution of sodium chloride. The organic layer is fractionated, allowed to dry on anhydrous sodium sulfate, filtrated and concentrated to obtain crude product.

Purified product having the melting point of 251 to 253° C. is obtained through recrystalization from dioxane.

Mass spectrum: m/z 288(M++1, 18%), 287(M+, 100), 256(15), 244(15), 202(24), 175(19), 144(41), 137(18), 116(14), 98(34), 89(14), 85(12);

Ultraviolet absorption spectrum (ethanol): λ max(nm) 368 (ε max 51,000).

Example 13

Synthesis of 6-methyl-3-(4-n-propoxycarbonylphenylaminomethylene)-2H,3H,4H-pyran-2,4-dione [compound represented by the general formula (I) of which A is (b), R$^3$=methyl and R=n-propyl]

Title compound was synthesized from 4-hydroxy-6-methyl-2-pyrone and 4-n-propyloxycarbonyl-N-formanilide using the same reaction conditions and after-treatment used in EXAMPLE 12.

Purified product having the melting point of 199 to 200° C. was obtained through recrystalization from dioxane.

Mass spectrum: m/z 316(M++1, 22%), 315(M+, 100), 273(28), 272(13), 256(33), 230(14), 172(11), 144(27), 137(15), 98(26), 89(10), 85(10);

Ultraviolet absorption spectrum (ethanol): λ max(nm) 368 (ε max 48,300).

Example 14

Synthesis of 6-methyl-3-(4-n-butoxycarbonylphenylaminomethylene)-2H,3H,4H-pyran-2,4-dione [compound represented by the general formula (I) of which A is (b), R$^3$=methyl and R=n-butyl]

Title compound was synthesized from 4-hydroxy-6-methyl-2-pyrone and 4-n-butyloxycarbonyl-N-formanilide using the same reaction conditions and after-treatment used in EXAMPLE 12.

Purified product having the melting point of 176.5 to 177° C. was obtained through recrystalization from dioxane.

Mass spectrum: m/z 330(M++1, 21%), 329(M+, 100), 274(12), 273(73), 256(33), 188(11), 172(11), 161(12), 144(26), 137(15), 98(26), 89(10), 85(10);

Ultraviolet absorption spectrum (ethanol): λ max(nm) 368 (ε max 77,900).

Example 15

Synthesis of 6-methyl-3-(4-n-octadecyloxycarbonylphenylaminomethylene)-2H,3H,4H-pyran-2,4-dione [compound represented by the general formula (I) of which A is (b), R$^3$=methyl and R=n-octadecyl]

Title compound was synthesized from 4-hydroxy-6-methyl-2-pyrone and 4-n-octadecyloxycarbonyl-N-formanilide using the same reaction conditions and after-treatment used in EXAMPLE 12.

Purified product having the melting point of 137 to 138.5° C. was obtained through recrystalization from toluene.

Mass spectrum: m/z 525(M++1, 100%), 524(10), 496(17), 482(15), 468(19), 454(15), 440(14), 426(14), 412(12), 387(13), 385(10), 384(11), 370(11), 356(11), 342(12), 328(12), 275(14), 274(69), 273(68), 257(38), 256(56), 230(17), 229(67), 172(15), 165(11), 146(11), 144(18), 138(13), 137(32), 120(22), 117(12), 97(12), 91(19);

Ultraviolet absorption spectrum (chloroform): λ max(nm) 372 (ε max 30,200).

Example 16

Synthesis of 6-methyl-3-[4-(2-ethylhexyloxycarbonylphenyl)-aminomethylene]-2H,3H,4H-pyran-2,4-dione [compound represented by the general formula (I) of which A is (b), R$^3$=methyl and R=2-ethylhexyl]

Title compound was synthesized from 4-hydroxy-6-methyl-2-pyrone and 4-(2-etylhexyloxycarbonyl)-N-formanilide using the same reaction conditions and after-treatment used in EXAMPLE 12.

Purified product having the melting point of 173.5 to 174.5° C. was obtained through recrystalization from toluene.

Mass spectrum: m/z 3850(M++1, 35%), 274(21), 273(100), 256(34), 188(6), 172(9), 144(8);

Ultraviolet absorption spectrum (chloroform): λ max(nm) 373 (ε max 34,300).

Example 17

Practical examples of formulation of skin ointment according to the present invention hereunder will be described.

According to the formulation listed in Table 4, a cosmetic liquid containing the compound according to EXAMPLE 16, that is 6-methyl-3-[4-(2-ethylhexyloxycarbonylphenyl)-aminomethylene]-2H,3H,4H-pyran-2,4-dione and as control cosmetic liquids, cosmetic liquids containing compound of Control 1, that is 2,2',4,4'-tetrahydroxybenzophenone, and compound of Control 2, that is 2-ethylhexyl p-methoxycinnamate, respectively, were prepared.

TABLE 4

| Composition | EXAMPLE 17 | Control 1 | Control 2 |
|---|---|---|---|
| ethanol | 8.0 | 8.0 | 8.0 |
| glycerin | 2.0 | 2.0 | 2.0 |
| citric acid | 0.02 | 0.02 | 0.02 |
| sodium citrate | 0.1 | 0.1 | 0.1 |
| methylparaben | 0.05 | 0.05 | 0.05 |
| POE hardened caster oil | 0.5 | 0.5 | 0.5 |
| perfume | some | some | some |
| compound of EXAMPLE 16 | 1.0 | — | — |
| compound of Control 1 | — | 1.0 | — |
| compound of Control 2 | — | — | 1.0 |
| propylene glycol | 7.0 | 7.0 | 7.0 |
| purified water | rest | rest | rest |

Control 1 exhibited pale yellow and was not suitable for cosmetic liquid.

Confirmation of Sunscreening Effect

Cosmetic liquid according to EXAMPLE 17 in which compound produced according to EXAMPLE 16 and that of Control 2 were, respectively, applied on the skin and their effect at practical use in beach was tested. On each of right or left half area of the back of ten respective male and female, each sample solution was applied, and the degree of suntan was examined and obtained results was listed in Table 5. Above described estimation criteria was used.

TABLE 5

| Estimation criteria: | Area applied with EXAMPLE 17 | Area applied with Control 2 |
|---|---|---|
| ◯ | 20 | 12 |
| Δ | 0 | 6 |
| Δ – × | 0 | 2 |
| × | 0 | 0 |
| Frequency of skin trouble | No | itching 7 cases slight rash 1 case |

Example 18

Light Stability Effect for Polymer Materials

Each of 0.05, 0.2 and 0.5 part by weight of sample produced according to EXAMPLE 16 was formulated with 100 parts by weight of polyethylene powder or polypropylene powder, mixed well using a mixer, then melted and kneaded using a extruder having the diameter of 25 mm at cylinder temperature of 200° C., and pelletized. Obtained pellets were compacted into sheets of 0.25 mm thickness at 210° C. to prepare test strips. Obtained test strips were punched into dumbbell shapes accommodating to a tension test. Test strip of control which did not contain light stabilizing agent was prepared, using the above described same method, and test strips were examined.

Using the WEL-75XS-HS-BEC model xenon sunshine long-life weatherometer manufactured by Suga Shiken-Kiki Co. Ltd., these test strips were light-irradiated with black panel temperature of 80° C., and were examined for lowering in tensile strength over time.

The tension test and calculation of tension strength was performed according above described methods.

Obtained results were as listed in Table 6. As apparent from the results shown in Table 6, the aminomethylene pyrone derivatives according to the present invention show prominent stabilizing effect (that is, elongated time to deterioration).

TABLE 6

| | (unit: kgf) | | | | | |
|---|---|---|---|---|---|---|
| Name of resin | 200 hrs | 400 hrs | 600 hrs | 800 hrs | 1000 hrs | 1200 hrs |
| Polypropylene: no, | 3.15 | 2.13 | 0 | — | — | — |
| 0.05 (wt%) | 3.40 | 3.34 | 2.98 | — | — | — |
| 0.2 (wt%) | 3.65 | 3.49 | 3.23 | — | — | — |
| 0.5 (wt%) | 3.85 | 3.62 | 3.42 | — | — | — |
| Polyethylene: no, | 2.42 | 2.29 | 2.25 | 2.10 | 1.90 | 0 |
| 0.05 (wt%) | 2.50 | 2.47 | 2.44 | 2.42 | 2.23 | 2.20 |
| 0.2 (wt%) | 2.58 | 2.50 | 2.49 | 2.44 | 2.37 | 2.31 |
| 0.5 (wt%) | 2.66 | 2.59 | 2.55 | 2.51 | 2.41 | 2.38 |

Example 19

Synthesis of 1,3-dimethyl-5-(4-methoxycarbonylphenyl)-aminomethylene-barbituric acid [compound represented by the general formula (I) of which A is (c), $R^4=R^5$=methyl and R=methyl]

After stirring suspension containing 0.20 mol of 1,3-dimethyl barbituric acid, 0.50 mol of 4-methoxycarbonyl-N-formanilide and 25 ml of toluene (solvent), 0.50 mol of phosphorus oxychloride is added to the suspension over 15 minutes. During the addition, temperature is maintained at 45° C. or lower. The suspension is further stirred for 10 minutes, then 250 ml of hot solution of toluene containing 0.48 mol of 1,3-dimethyl barbituric acid is added to at 60 to 65° C., over 45 minutes. The reaction mixture is constantly stirred and allowed to cool to room temperature, and reaction is terminated by adding the reaction mixture dropwise into 600 ml of 15% sodium hydroxide solution. Obtained organic layer is being washed with 200 ml of saturated aqueous solution of sodium chloride. The organic layer is fractionated, allowed to dry on anhydrous sodium sulfate, filtrated and concentrated to obtain crude product.

Purified product having the melting point of 239.5 to 240.5 t is obtained through recrystalization from ethanol/dioxane.

Ultraviolet absorption spectrum (ethanol): λ max(nm) 352, (ε max 49,000).

Example 20

Synthesis of 1,3-dimethyl-5-(4-n-propoxycarbonylphenyl)-aminomethylene-barbituric acid [compound represented by the general formula (I) of which A is (c), $R^4=R^5$=methyl and R=n-propyl]

Title compound was synthesized from 1,3-dimethyl barbituric acid and 4-n-propyloxycarbonyl-N-formanilide using the same reaction conditions and after-treatment used in EXAMPLE 19.

Purified product having the melting point of 150 to 151° C. was obtained through recrystalization from ethanol/dioxane.

Ultraviolet absorption spectrum (ethanol): λ max(nm) 354 (ε max 48,400).

Example 21

Synthesis of 1,3-dimethyl-5-(4-n-butoxycarbonylphenyl)-aminomethylene-barbituric acid

[compound represented by the general formula (I) of which A is (c), $R^4=R^5$=methyl and R=n-butyl]

Title compound was synthesized from 1,3-dimethyl barbituric acid and 4-n-butyloxycarbonyl-N-formanilide using the same reaction conditions and after-treatment used in EXAMPLE 19.

Purified product having the melting point of 139 to 140° C. was obtained through recrystalization from ethanol/dioxane.

Ultraviolet absorption spectrum (ethanol): λ max(nm) 353 (ε max 47,800).

Example 22

Synthesis of 1,3-dimethyl-5-(4-n-octadecyloxycarbonyl-phenyl)aminomethylene-barbituric acid [compound represented by the general formula (I) of which A is (c), $R^4=R^5$=methyl and R=n-octadecyl]

Title compound was synthesized from 1,3-dimethyl barbituric acid and 4-n-octadecyloxycarbonyl-N-formanilide using the same reaction conditions and after-treatment used in EXAMPLE 19.

Purified product having the melting point of 116.5 to 117.5° C. was obtained through recrystalization from toluene.

Ultraviolet absorption spectrum (chloroform): λ max(nm) 356 (ε max 38,800).

Example 23

Synthesis of 1,3-dimethyl-5- {N-[4-(2-ethylhexyl)oxycarbonylphenyl]aminomethylene} barbituric acid [compound represented by the general formula (I) of which A is (c), $R^4=R^5$=methyl and R=2-ethylhexyl]

Title compound was synthesized from 1,3-dimethyl barbituric acid and 4-(2-ethylhexyl)oxycarbonyl-N-formanilide using the same reaction conditions and after-treatment used in EXAMPLE 19.

Purified product having the melting point of 164.5 to 165.5° C. was obtained through recrystalization from toluene.

Ultraviolet absorption spectrum (ethanol): λ max(nm) 356 (ε max 40,700).

Example 24

Practical examples of formulation of skin ointment according to the present invention hereunder will be described.

According to the formulation listed in Table 7, a cosmetic liquid containing the compound according to EXAMPLE 23, that is 1,3-dimethyl-5- {N-[4-(2-ethylhexyl)oxycarbonylphenyl]-aminomethylene} barbituric acid and as control cosmetic liquids, cosmetic liquids containing compound of Control 1, that is 2,2',4,4'-tetrahydroxybenzophenone, and compound of Control 2, that is 2-ethylhexyl p-methoxycinnamate, respectively, were prepared.

TABLE 71

| Composition | EXAMPLE 24 | Control 1 | Control 2 |
| --- | --- | --- | --- |
| ethanol | 8.0 | 8.0 | 8.0 |
| glycerin | 2.0 | 2.0 | 2.0 |
| citric acid | 0.02 | 0.02 | 0.02 |

TABLE 71-continued

| Composition | EXAMPLE 24 | Control 1 | Control 2 |
| --- | --- | --- | --- |
| sodium citrate | 0.1 | 0.1 | 0.1 |
| methylparaben | 0.05 | 0.05 | 0.05 |
| POE hardened caster oil | 0.5 | 0.5 | 0.5 |
| perfume | some | some | some |
| compound of EXAMPLE 23 | 1.0 | — | — |
| compound of Control 1 | — | 1.0 | — |
| compound of Control 2 | — | — | 1.0 |
| propylene glycol | 7.0 | 7.0 | 7.0 |
| purified water | rest | rest | rest |

Control 1 exhibited pale yellow and was not suitable for cosmetic liquid.

Confirmation of Sunscreening Effect

Composition prepared in EXAMPLE 23 and cosmetic liquid according to Control 2 were, respectively, applied on the skin and their effect at practical use in beach was tested. On each of right or left half area of the back of ten respective male and female, each sample solution was applied, and the degree of suntan was examined and obtained results was listed in Table 8. Estimation was performed according to above described estimation criteria.

TABLE 8

| Estimation criteria | Area applied with EXAMPLE 24 | Area applied with control 2 |
| --- | --- | --- |
| ○ | 18 | 12 |
| Δ | 2 | 6 |
| Δ – × | 0 | 2 |
| × | 0 | 0 |
| Frequency of skin trouble | No | itching 7 cases slight rash 1 case |

Example 25

Light Stability Effect for Polymer Materials

Each of 0.05, 0.2 and 0.5 part by weight of sample produced according to EXAMPLE 23 was formulated with 100 parts by weight of polyethylene powder or polypropylene powder, mixed well using a mixer, then melted and kneaded using a extruder having the diameter of 25 mm at cylinder temperature of 200° C., and pelletized. Obtained pellets were compacted into sheets of 0.25 mm thickness at 210° C. to prepare test strips. Obtained test strips were punched into dumbbell shapes accommodating to a tension test. Test strip of control which did not contain light stabilizing agent was prepared, using the above described same method, and test strips were examined.

Using the WEL-75XS-HS-BEC model xenon sunshine long-life weatherometer manufactured by Suga Shiken-Kiki Co. Ltd., these test strips were light-irradiated with black panel temperature of 80° C., and were examined for lowering in tensile strength over time.

The tension test and calculation of tension strength was performed according above described methods.

Obtained results were as listed in Table 9. As apparent from the results shown in Table 9, the aminomethylene barbituric acid derivatives according to the present invention show prominent stabilizing effect (that is, elongated time to deterioration).

TABLE 9

| Name of risin | (unit: kgf) | | | | | |
|---|---|---|---|---|---|---|
| | 200 hrs | 400 hrs | 600 hrs | 800 hrs | 1000 hrs | 1200 hrs |
| Polypropylene: no, | 3.15 | 2.13 | 0 | — | — | — |
| 0.05 (wt%) | 3.58 | 3.07 | 2.91 | — | — | — |
| 0.2 (wt%) | 3.72 | 3.46 | 3.38 | — | — | — |
| 0.5 (wt%) | 3.98 | 3.82 | 2.64 | — | — | — |
| Polyethylene: no, | 2.42 | 2.29 | 2.25 | 2.10 | 1.90 | 0 |
| 0.05 (wt%) | 2.68 | 2.58 | 2.50 | 2.48 | 2.32 | 2.22 |
| 0.2 (wt%) | 2.83 | 2.70 | 2.62 | 2.38 | 2.42 | 2.38 |
| 0.5 (wt%) | 2.88 | 2.80 | 2.76 | 2.70 | 2.64 | 2.60 |

Example 26

Synthesis of 3-[4-(2-ethylhexyloxycarbonyl)phenylaminomethylene]chroman-2,4-dione [compound represented by the general formula (I) of which A is (d), $R^6$=hydrogen atom, n=1 and R=2-ethylhexyl]

After stirring suspension containing 0.20 mol of 4-hydroxy coumarin, 0.50 mol of 4-(2-ethylhexyloxycarbonyl)-N-formanilide and 25 ml of toluene, 0.50 mol of phosphorus oxychloride is added to the suspension over 15 minutes. During the addition, temperature is maintained at 45° C. or lower. The suspension is further stirred for 10 minutes, then 250 ml of hot solution of toluene containing 0.48 mol of 4-hydroxy coumarin is added to at 60 to 65° C., over 45 minutes. The reaction mixture is constantly stirred and allowed to cool to room temperature, and reaction is terminated by adding the reaction mixture dropwise into 600 ml of 15% sodium hydroxide solution. Obtained organic layer is being washed with 200 ml of saturated aqueous solution of sodium chloride. The organic layer is fractionated, allowed to dry on anhydrous sodium sulfate, filtrated and concentrated to obtain crude product.

Purified product having the melting point of 179 to 180° C. is obtained through recrystalization from dioxane.

Ultraviolet absorption spectrum (chloroform): λ max(nm) 375 (ε max 38,500);

Infrared absorption spectrum: $cm^{-1}$ (KBr) 3420 (NH), 1708 (ester and lactone C=O), 1642 (4-position C=O), 1630 (—NH—CH=C=), 1280 (C—O—C).

Example 27

Synthesis of 3-(4-ethoxycarbonylphenylaminomethylene)chroman-2,4-dione [compound represented by the general formula (I) of which A is (d), $R^6$=hydrogen atom, n=1 and R=ethyl]

Same procedure used in EXAMPLE 26, except that 4-ethoxycarbonyl-N-formanilide was used instead of 4-(2-ethylhexyloxycarbonyl)-N-formanilide, was repeated.

Melting point: 233 to 234° C.;

Ultraviolet absorption spectrum (chloroform): λ max(nm) 374, (ε max 38,200);

Infrared absorption spectrum: $cm^{-1}$ (KBr) 3430 (NH), 1718 (ester and lactone C=O), 1650 (4-position C=O), 1638 (—NH—CH=C=), 1278 (C—O—C).

Example 28

Synthesis of 3-(4-n-propoxycarbonylphenylaminomethylene)chroman-2,4-dione [compound represented by the general formula (I) of which A is (d), $R^6$=hydrogen atom, n=1 and R=n-propyl]

Same procedure used in EXAMPLE 26, except that 4-n-propoxycarbonyl-N-formanilide was used instead of 4-(2-ethylhexyloxycarbonyl)-N-formanilide, was repeated.

Melting point: 211.5 to 212.5° C.

Ultraviolet absorption spectrum (chloroform): λ max(nm) 375 (ε max 37,600);

Infrared absorption spectrum: $cm^{-1}$ (KBr) 3430 (NH), 1718 (ester and lactone C=O), 1650 (4-position C=O), 1630 (—NH—CH=C=), 1278 (C—O—C).

Example 29

Synthesis of 3-(4-isopropoxycarbonylphenylaminomethylene)chroman-2,4-dione [compound represented by the general formula (I) of which A is (d), $R^6$=hydrogen atom, n=1 and R=isopropyl]

Same procedure used in EXAMPLE 26, except that 4-isopropoxycarbonyl-N-formanilide was used instead of 4-(2-ethylhexyloxycarbonyl)-N-formanilide, was repeated.

Melting point: 206.5 to 207° C.;

Ultraviolet absorption spectrum (chloroform): λ max(nm) 374 (ε max 35,600);

Infrared absorption spectrum: $cm^{-1}$ (KBr) 3430 (NH), 1710 (ester and lactone C=O), 1650 (4-position C=O), 1630 (—NH—CH=C=), 1278 (C—O—C).

Example 30

Synthesis of 3-(4-n-butoxycarbonylphenylaminomethylene)chroman-2,4-dione [compound represented by the general formula (I) of which A is (d), $R^6$=hydrogen atom, n=1 and R=n-butyl]

Same procedure used in EXAMPLE 26, except that 4-n-butoxycarbonyl-N-formanilide was used instead of 4-(2-ethylhexyloxycarbonyl)-N-formanilide, was repeated.

Melting point: 207 to 207.5° C.;

Ultraviolet absorption spectrum (chloroform): λ max(nm) 375 (ε max 38,400);

Infrared absorption spectrum: $cm^{-1}$ (KBr) 3430 (NH), 1720 (ester and lactone C=O), 1650 (4-position C=O), 1630 (—NH—CH=C=), 1275 (C—O—C).

Example 31

Synthesis of 3-(4-isobutoxycarbonylphenylaminomethylene)chroman-2,4-dione [compound represented by the general formula (I) of which A is (d), $R^6$=hydrogen atom, n=1 and R=isobutyl]

Same procedure used in EXAMPLE 26, except that 4-isobutoxycarbonyl-N-formanilide was used instead of 4-(2-ethylhexyloxycarbonyl)-N-formanilide, was repeated.

Melting point: 221.5 to 222.5° C.;

Ultraviolet absorption spectrum (chloroform): λ max(nm) 376 (ε max 38,000)

Infrared absorption spectrum: $cm^{-1}$ (KBr) 3440 (NH), 1718 (ester and lactone C=O), 1650 (4-position C=O), 1628 (—NH—CH=C=), 1272 (C—O—C).

Example 32

Practical examples of formulation of skin ointment according to the present invention hereunder will be described.

According to the formulation listed in Table 10, a cosmetic liquid containing the compound according to EXAMPLE 26, that is 3-[4-(2-ethylhexyloxycarbonyl)

phenylaminomethylene]chroman-2,4-dione and as control cosmetic liquids, cosmetic liquids containing compound of Control 1, that is 2,2',4,4'-tetrahydroxybenzophenone, and compound of Control 2, that is 2-ethylhexyl p-methoxycinnamate, respectively, were prepared.

TABLE 10

| Composition | EXAMPLE 32 | Control 1 | Control 2 |
|---|---|---|---|
| ethanol | 8.0 | 8.0 | 8.0 |
| glycerin | 2.0 | 2.0 | 2.0 |
| citric acid | 0.02 | 0.02 | 0.02 |
| sodium citrate | 0.1 | 0.1 | 0.1 |
| methylparaben | 0.05 | 0.05 | 0.05 |
| POE hardened caster oil | 0.5 | 0.5 | 0.5 |
| perfume | some | some | some |
| compound of EXAMPLE 26 | 1.0 | — | — |
| compound of Control 1 | — | 1.0 | — |
| compound of Control 2 | — | — | 1.0 |
| propylene glycol | 7.0 | 7.0 | 7.0 |
| purified water | rest | rest | rest |

Control 1 exhibited pale yellow and was not suitable for cosmetic liquid.

Example 33
Confirmation of Sunscreening Effect

Cosmetic liquid of the present invention, containing the compound produced according to EXAMPLE 30, in stead of compound produced according to EXAMPLE 26 which was used in EXAMPLE 32, and cosmetic liquid according to Control 2 were, respectively, applied on the skin and their effect at practical use in beach was tested. On each of right or left half area of the back of ten respective male and female, each sample solution was applied, and the degree of suntan was examined and obtained results was listed in Table 11. Estimation was performed according to above described estimation criteria.

TABLE 11

| Estimation criteria | Area applied with EXAMPLE 33 | Area applied with Control 2 |
|---|---|---|
| ○ | 19 | 17 |
| Δ | 1 | 2 |
| Δ – × | 0 | 1 |
| × | 0 | 0 |
| Frequency of skin trouble | No | itching 3 cases slight rash 1 case |

Example 34
Light Stability Effect for Polymer Materials

Each of 0.05, 0.2 and 0.5 part by weight of sample produced according to EXAMPLE 26 was formulated with 100 parts by weight of polyethylene powder or polypropylene powder, mixed well using a mixer, then melted and kneaded using a extruder having the diameter of 25 mm at cylinder temperature of 200° C., and pelletized. Obtained pellets were compacted into sheets of 0.25 mm thickness at 210° C., to prepare test strips. Obtained test strips were punched into dumbbell shapes accommodating to a tension test. Test strip of control which did not contain light stabilizing agent was prepared, using the above described same method, and test strips were examined.

Using the WEL-75XS-HS-BEC model xenon sunshine long-life weatherometer manufactured by Suga Shiken-Kiki Co. Ltd., these test strips were light-irradiated with black panel temperature of 80° C., and were examined for lowering in tensile strength over time.

The tension test and calculation of tension strength was performed according above described methods.

Obtained results were as listed in Table 12. As apparent from the results shown in Table 12, the aminomethylene chroman derivatives according to the present invention show prominent stabilizing effect (that is, elongated time to deterioration).

TABLE 12

| | (unit: kgf) | | | | | |
|---|---|---|---|---|---|---|
| Name of resin | 200 hrs | 400 hrs | 600 hrs | 800 hrs | 1000 hrs | 1200 hrs |
| Polypropylene: no, | 3.15 | 2.13 | 0 | — | — | — |
| 0.05 (wt%) | 3.56 | 3.04 | 2.90 | — | — | — |
| 0.2 (wt%) | 3.70 | 3.40 | 3.36 | — | — | — |
| 0.5 (wt%) | 3.92 | 3.81 | 3.60 | — | — | — |
| Polyethylene: no, | 2.42 | 2.26 | 2.25 | 2.10 | 1.90 | 0 |
| 0.05 (wt%) | 2.82 | 2.72 | 2.60 | 2.63 | 2.50 | 2.40 |
| 0.2 (wt%) | 2.80 | 2.92 | 2.80 | 2.74 | 258 | 2.60 |
| 0.5 (wt%) | 3.02 | 3.02 | 2.92 | 2.80 | 2.70 | 2.80 |

Example 35

Synthesis of 2,2-dimethyl-5-[4-(2-ethylhexyloxycarbonyl)phenylaminomethylene]-1,3-dioxane-4,6-dione [compound represented by the general formula (I) of which A is (e), $R^7=R^8$=methyl and R=2-ethylhexyl]

After stirring suspension containing 0.20 mol of Meldrum's acid, 0.50 mol of 4-(2-ethylhexyloxycarbonyl)-N-formanilide and 25 ml of toluene, 0.50 mol of phosphorus oxychloride is added to the suspension over 15 minutes. During the addition, temperature is maintained at 45° C. or lower. The suspension is further stirred for 10 minutes, then 250 ml of hot solution of toluene containing 0.30 mol of Meldrum's acid is added to at 60 to 65° C., over 45 minutes. The reaction mixture is constantly stirred and allowed to cool to room temperature, and reaction is terminated by adding the reaction mixture dropwise into 600 ml of 15% sodium hydroxide solution. Obtained organic layer is being washed with 200 ml of saturated aqueous solution of sodium chloride. The organic layer is fractionated, allowed to dry on anhydrous sodium sulfate, filtrated and concentrated to obtain crude product.

Purified product having the melting point of 148.5 to 149.5° C. is obtained through recrystalization from dioxane.

Ultraviolet absorption spectrum (chloroform): λ max(nm) 339,

ε max 35,500;

Infrared absorption spectrum (chloroform): $cm^{-1}$ (KBr) 3420(NH), 1708 (ester and lactone C=O ), 1642 (4-position C=O ), 1630 (—NH—CH=C=), 1280 (C—O—C).

Example 36

Synthesis of 2,2-dimethyl-5-(4-ethoxycarbonylphenylaminomethylene)-1,3-dioxane-4,6-dione [compound represented by the general formula (I) of which A is (e), $R^7=R^8$=methyl and R=ethyl]

Same procedure used in EXAMPLE 35, except that 4-ethoxycarbonyl-N-formanilide was used instead of 4-(2-ethylhexyloxycarbonyl)-N-formanilide, was repeated.

Melting point: 184 to 184.5° C.;

Ultraviolet absorption spectrum (chloroform): λ max (nm) 338,

ε max 35,700;

Infrared absorption spectrum: $cm^{-1}$ (KBr) 3220 (NH), 1730 (lactone C=O ), 1718 (ester C=O ), 1688 (4-position C=O ), 1652 (—NH—CH=C=).

Example 37

Synthesis of 2,2-dimethyl-5-(4-n-propoxycarbonylphenylaminomethylene)-1,3-dioxane-4,6-dione [compound represented by the general formula (I) of which A is (e), $R^7=R^8$=methyl and R=n-propyl]

Same procedure used in EXAMPLE 35, except that 4-(n-proxycarbonyl)-N-formanilide was used instead of 4-(2-ethylhexyloxycarbonyl)-N-formanilide, was repeated.

Melting point: 154 to 155° C.;

Ultraviolet absorption spectrum (chloroform): λ max (nm) 337,

ε max max 35,900;

Infrared absorption spectrum: $cm^{-1}$ (KBr) 3229 (NH), 1732 (lactone C=O ), 1718 (ester C=O ), 1682 (4-position C=O ), 1638 (—NH—CH=C=).

Example 38

Synthesis of 2,2-dimethyl-5-(4-isopropoxycarbonylphenylaminomethylene)-1,3-dioxane-4,6-dione [compound represented by the general formula (I) of which A is (e), $R^7=R^8$=isopropyl and R=isopropyl]

Same procedure used in EXAMPLE 35, except that 4-(isoproxycarbonyl)-N-formanilide was used instead of 4-(2-ethylhexyloxycarbonyl)-N-formanilide, was repeated.

Melting point: 185 to 186° C.;

Ultraviolet absorption spectrum (chloroform): λ max(nm) 338,

ε max 35,200;

Infrared absorption spectrum: $cm^{-1}$ (KBr) 3220 (NH), 1736 (lactone C=O ), 1718 (ester C=O ), 1682 (4-position C=O ), 1640 (—NH—CH=C=).

Example 39

Synthesis of 2,2-dimethyl-5-(4-n-butoxycarbonylphenylaminomethylene)-1,3-dioxane-4,6-dione [compound represented by the general formula (I) of which A is (e), $R^7=R^8$=methyl and R=n-butyl]

Same procedure used in EXAMPLE 35, except that 4-(n-butoxycarbonyl)-N-formanilide was used instead of 4-(2-ethylhexyloxycarbonyl)-N-formanilide, was repeated.

Melting point: 161 to 162° C.;

Ultraviolet absorption spectrum (chloroform): λ max(nm) 338,

ε max 35,200;

Infrared absorption spectrum: $cm^{-1}$ (KBr) 3220 (NH), 1738 (lactone C=O ), 1716 (ester C=O ), 1680 (4-position C=O ), 1630 (—NH—CH=C=).

Example 40

Synthesis of 2,2-dimethyl-5-(4-isobutoxycarbonylphenylaminomethylene)-1,3-dioxane-4,6-dione [compound represented by the general formula (I) of which A is (e), $R^7=R^8$=methyl and R=isobutyl]

Same procedure used in EXAMPLE 35, except that 4-(isobutoxycarbonyl)-N-formanilide was used instead of 4-(2-ethylhexyloxycarbonyl)-N-formanilide, was repeated.

Melting point: 186.5 to 187.5° C.;

Ultraviolet absorption spectrum (chloroform): λ max(nm) 338,

ε max 43,400;

Infrared absorption spectrum: $cm^{-1}$ (KBr) 3220 (NH), 1732 (lactone C=O ), 1705 (ester C=O ), 1680 (4-position C=O ), 1632 (—NH—CH=C=).

Example 41

Practical examples of formulation of skin ointment according to the present invention hereunder will be described.

According to the formulation listed in Table 13, a cosmetic liquid containing the compound according to EXAMPLE 35, that is 2,2-dimethyl-5-[4-(2-ethylhexyloxycarbonyl)phenylaminomethylene]-1,3-dioxane-4,6-dione and as control cosmetic liquids, cosmetic liquids containing compound of Control 1, that is 2,2',4,4'-tetrahydroxybenzophenone, and compound of Control 2, that is 2-ethylhexyl p-methoxycinnamate, respectively, were prepared.

TABLE 13

| Composition | EXAMPLE 41 | Control 1 | Control 2 |
|---|---|---|---|
| ethanol | 8.0 | 8.0 | 8.0 |
| glycerin | 2.0 | 2.0 | 2.0 |
| citric acid | 0.02 | 0.02 | 0.02 |
| sodium citrate | 0.1 | 0.1 | 0.1 |
| methylparaben | 0.05 | 0.05 | 0.05 |
| POE hardened caster oil | 0.5 | 0.5 | 0.5 |
| perfume | some | some | some |
| compound of EXAMPLE 35 | 1.0 | — | — |
| compound of Control 1 | — | 1.0 | — |
| compound of Control 2 | — | — | 1.0 |
| propylene glycol | 7.0 | 7.0 | 7.0 |
| purified water | rest | rest | rest |

Control 1 exhibited pale yellow and was not suitable for cosmetic liquid.

Example 42

Confirmation of Sunscreening Effect

Cosmetic liquid of the present invention, containing the compound produced according to EXAMPLE 39, in stead of compound produced according to EXAMPLE 35 which was used in EXAMPLE 41, and cosmetic liquid according to Control 2 were, respectively, applied on the skin and their effect at practical use in beach was tested. On each of right or left half area of the back of ten respective male and female, each sample solution was applied, and the degree of suntan was examined and obtained results was listed in Table 14. Estimation was performed according to above described estimation criteria.

TABLE 14

| Estimation criteria | Area applied with EXAMPLE 41 | Area applied with Control 2 |
|---|---|---|
| ○ | 18 | 17 |
| Δ | 1 | 2 |

TABLE 14-continued

| Estimation criteria | Area applied with EXAMPLE 41 | Area applied with Control 2 |
|---|---|---|
| Δ – × | 1 | 1 |
| × | 0 | 0 |
| Frequency of skin trouble | itching 1 case | itching 3 cases slight rash 1 case |

Example 43

Light Stability Effect for Polymer Materials

Each of 0.05, 0.2 and 0.5 part by weight of sample produced according to EXAMPLE 35 was formulated with 100 parts by weight of polyethylene powder or polypropylene powder, mixed well using a mixer, then melted and kneaded using a extruder having the diameter of 25 mm at cylinder temperature of 200° C., and pelletized. Obtained pellets were compacted into sheets of 0.25 mm thickness at 210° C. to prepare test strips. Obtained test strips were punched into dumbbell shapes accommodating to a tension test. Test strip of control which did not contain light stabilizing agent was prepared, using the above described same method, and test strips were examined.

Using the WEL-75XS-HS-BEC model xenon sunshine long-life weatherometer manufactured by Suga Shiken-Kiki Co.Ltd., these test strips were light-irradiated with black panel temperature of 80° C., and were examined for lowering in tensile strength over time.

The tension test and calculation of tension strength was performed according above described methods.

Obtained results were as listed in Table 15. As apparent from the results shown in Table 15, the aminomethylene chroman derivatives according to the present invention show prominent stabilizing effect (that is, elongated time to deterioration).

TABLE 15

| | (unit: kgf) | | | | | |
|---|---|---|---|---|---|---|
| Name of resin | 200 hrs | 400 hrs | 600 hrs | 800 hrs | 1000 hrs | 1200 hrs |
| Polypropylene: no, | 3.15 | 2.13 | 0 | — | — | — |
| 0.05 (wt%) | 3.68 | 3.17 | 3.01 | — | — | — |
| 0.2 (wt%) | 3.76 | 3.44 | 3.36 | — | — | — |
| 0.5 (wt%) | 3.96 | 3.80 | 3.62 | — | — | — |
| Polyethylene: no, | 2.42 | 2.29 | 2.25 | 2.10 | 1.90 | 0 |
| 0.05 (wt%) | 2.86 | 2.76 | 2.68 | 2.66 | 2.50 | 2.21 |
| 0.2 (wt%) | 2.81 | 2.88 | 2.80 | 2.76 | 2.60 | 2.39 |
| 0.5 (wt%) | 3.06 | 2.98 | 2.94 | 2.88 | 2,82 | 2.78 |

What is claimed is:

1. An aminomethylene derivative represented by general formula (I):

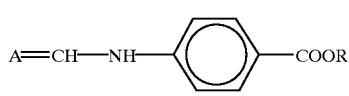
(I)

wherein A is a cyclic oxo group of following general formula (d):

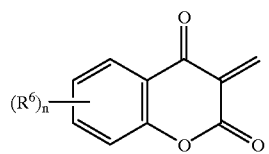
(d)

wherein $R^6$ is a group selected from the group consisting of linear or branched, saturated or unsaturated alkyl groups, cycloalkyl groups, aralkyl groups, aryl groups, alkoxy groups, alkoxycarbonyl groups, acyl groups, dialkylamino groups and halogens, and R is a group selected from the group consisting of linear or branched, saturated or unsaturated alkyl groups, aralkyl groups, aryl groups, cycloalkyl groups and alkoxycarbonylalkylene groups, and n is an integer of 0 to 4 wherein when n is 2 or more, each of plural $R^6$s can be different groups within the above-described groups.

2. A method for producing an aminomethylene derivative represented by general formula (I):

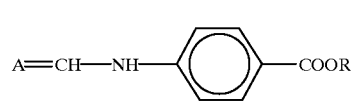
(I)

wherein A is following general formula (d):

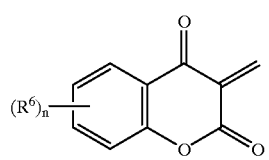
(d)

wherein $R^6$ is a group selected from the group consisting of linear or branched, saturated or unsaturated alkyl groups, cycloalkyl groups, aralkyl groups, aryl groups, alkoxy groups, alkoxycarbonyl groups, acyl groups, dialkylamino groups and halogens, and R is a group selected from the group consisting of linear or branched, saturated or unsaturated alkyl groups, aralkyl groups, aryl groups, cycloalkyl groups and alkoxycarbonylalkylene groups, and n is an integer of 0 to 4 wherein when n is 2 or more, each of plural $R^6$s can be different groups within the above-described groups, wherein a cyclic oxo compound represented by general formula (II):

A'  (II)

wherein A' is a compound of following general formula (d):

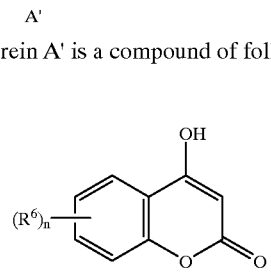
(d')

wherein $R^6$ is a group selected from the group consisting of linear or branched, saturated or unsaturated alkyl groups, cycloalkyl groups, aralkyl groups, aryl groups, alkoxy groups, alkoxycarbonyl groups, acyl groups, dialkylamino groups and halogens, and n is an integer of 0 to 4 wherein when n is 2 or more, each of plural $R^6$s can be different groups within the above-described groups, is allowed to react with an N-formylaminobenzoate derivative represented by general formula (III):

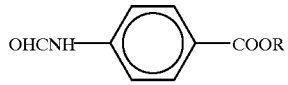

(III)

wherein R is a group selected from the group consisting of linear or branched, saturated or unsaturated alkyl groups, cycloalkyl groups, aralkyl groups, aryl groups and alkoxycarbonylalkylene groups, in an organic solvent and in the presence of a halide.

3. A method according to claim 2, wherein said halide is a chloride.

* * * * *